United States Patent [19]

Hayasi et al.

[11] Patent Number: 4,902,700

[45] Date of Patent: Feb. 20, 1990

[54] THIAZOLE DERIVATIVE AND LEUKOTRIENE ANTAGONIST CONTAINING THE SAME AS THE EFFECTIVE INGREDIENTS

[75] Inventors: Yosio Hayasi; Tomei Oguri, both of Ushiku; Masaki Shimoda, Ibaraki; Mikio Tsutsui, Ibaraki; Kazuo Takahashi, Ibaraki; Hitoshi Miida, Tsuchiura, all of Japan

[73] Assignee: Mitsubishi Kasei Corporation, Tokyo, Japan

[21] Appl. No.: 279,225

[22] Filed: Nov. 28, 1988

Related U.S. Application Data

[63] Continuation of Ser. No. 919,497, Oct. 16, 1986, abandoned.

[30] Foreign Application Priority Data

Oct. 16, 1985 [JP] Japan .................................. 60-228912

[51] Int. Cl.$^4$ .................. C07D 277/30; C07D 277/64; A61K 31/425
[52] U.S. Cl. ..................................... 514/365; 514/367; 548/163; 548/179; 548/180; 548/192; 548/201; 548/202; 548/203; 548/204; 548/205
[58] Field of Search ............... 548/179, 180, 703, 704, 548/205, 201, 202, 163, 192; 514/367, 365

[56] References Cited

U.S. PATENT DOCUMENTS 4,581,457  4/1986  Musser ................................ 548/179
4,594,425  6/1986  Musser ................................ 548/161

*Primary Examiner*—Robert Gerstl

*Attorney, Agent, or Firm*—Oblon, Spivak, McClelland, Maier & Neustadt

[57] ABSTRACT

Disclosed are a thiazole derivative represented by the following formula, a pharmaceutically acceptable salt thereof and leukotriene antagonist containing the same as the active ingredients:

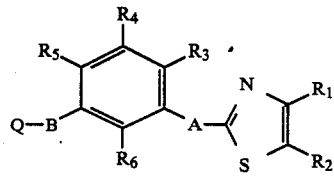

wherein $R_1$ and $R_2$ each independently represent a hydrogen atom, an alkyl group having 1 to 8 carbon atoms, a lower alkoxycarbonyl group or a substituted or unsubstituted phenyl group or cooperatively represent a tetramethylene group corresponding to a fused cyclohexane ring or a butadienylene group which is unsubstituted or substituted with a halogen atom, a lower alkoxy group, a lower alkoxycarbonyl group or an alkyl group having 1 to 3 carbon atoms corresponding to a fused benzene ring; $R_3$, $R_4$, $R_5$ and $R_6$ each independently represent a hydrogen atom, a hydroxyl group, a lower alkoxy group, an alkyl group having 1 to 3 carbon atoms or a halogen atom; A represents a linking group having 2 to 4 chain members; B represents a linking group having 2 to 5 chain members; and Q represents a carboxyl group, a lower alkoxy group, a hydroxyl group, an alkoxycarbonyl group having 2 to 6 carbon atoms or a 5-tetrazolyl group.

6 Claims, No Drawings

THIAZOLE DERIVATIVE AND LEUKOTRIENE ANTAGONIST CONTAINING THE SAME AS THE EFFECTIVE INGREDIENTS

This application is a Continuation of application Ser. No. 06/919,497, filed on Oct. 16, 1986, now abandoned.

BACKGROUND OF THE INVENTION

This invention relates to a novel thiazole derivative having leukotriene antagonistic action and a leukotriene antagonist containing the same as the active ingredient.

For prophylaxis or therapy of allergic diseases, there are the method which inhibits liberation of the mediator of anaphylaxis and the method which permits an antagonist to act on the mediator liberated. Disodium cromoglycate [The Merck Index, ninth edition 2585 (1976)] and Tranirast [Journal of Japanese Pharmacology, 74, 699 (1978)] are typical drugs belonging to the former and those belonging to the latter may include drugs antagonistic to hystamine which is one of the mediators of alllergic reactions such as diphenehydramine, chlorophenylamine, astemizole, terfenadine, clemastine, etc., as well known drugs. However, a substance which cannot be antagonized with an anti-hystamine agent, namely SRS (Slow Reacting Substance) has been suggested to be liberated from the lung of a bronchial asthma patient [Progr. Allergy, 6, 539 (1962)], and recently these SRS [leukotriene $C_4(LTC_4)$, leukotriene $D_4(LTD_4)$ and leukotriene $E_4(LTE_4)$] are comprehensively called SRS [Proc. Natl. Acad. Sci. U.S.A., 76, 4275 (1979) and 77, 2014 (1980); Nature, 285, 104 (1980)] and considered as the important factor participating in human asthma attack [Proc. Natl. Acad. Sci. U.S.A., 80, 1712 (1983)].

Some leukotriene antagonists have been known in patents or literatures. For example, there have been known FPL-55712 [Agents and Actions, 9, 133 (1979)] represented by the following formula:

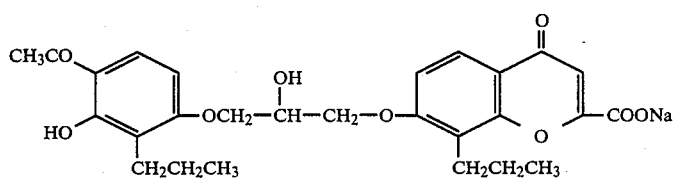

KC-404 [Jap. J. Pharm., 33, 267 (1983)] represented by the following formula:

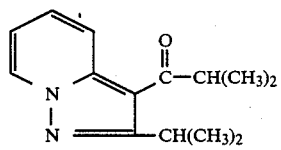

KZ-111 [Chem. Abst, registration number 72637-30-0] represented by the following formula:

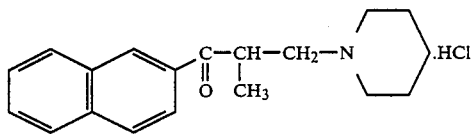

and the compound represented by the following formula (U.S. Pat. No. 4,296,129):

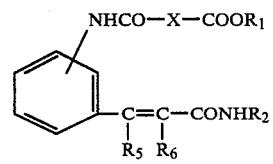

wherein $R_1$ represents a hydrogen atom, an alkyl group having 1 to 4 carbon atoms or a group represented by represented by the following formula:

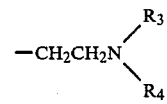

(wherein $R_3$ and $R_4$ each represent an alkyl group having 1 to 3 carbon atoms); $R_2$ represents an alkyl group having 8 to 15 carbon atoms or a cycloalkyl group having 6 to 12 carbon atoms; $R_5$ and $R_6$ each represent a hydrogen atom or a methyl group. However, none of these have been clinically applied.

On the other hand, of the thiazole derivatives, as the compounds in which the 2-position of thiazole and the phenyl group are bonded through 2 to 4 atoms, there have been known a large number of compounds such as the compound (Japanese Unexamine Patent Publication No. 22460/1973) represented by the formula:

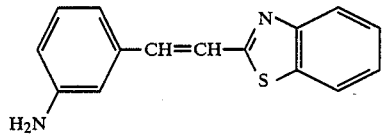

the compound represented by the following formula [Farmaco. Ed. Sci, 21, 740 (1966)]:

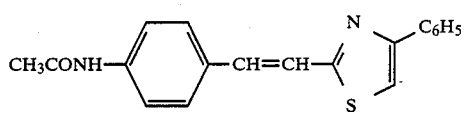

the compound represented by the following formula (German Pat. No. 31 48 291):

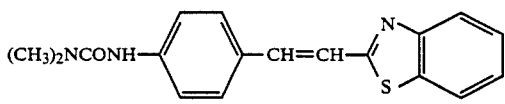

and the compound represented by the following formula (Japanese Unexamined Patent Publication No. 16871/1984):

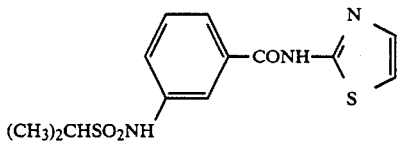

However, in any of these literatures or patents, nothing is mentioned about the leukotriene antagonistic action.

The present inventors have sought after compounds having antagonistic action to leukotriene and effective as the therapeutical medicine for various diseases caused by leukotriene, and consequently found that a novel thiazole derivative has excellent leukotriene antagonistic action to accomplish the present invention.

SUMMARY OF THE INVENTION

The thiazole derivative of the present invention is a compound represented by the following formula (I):

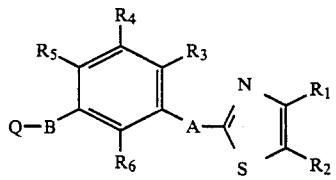

wherein $R_1$ and $R_2$ each independently represent a hydrogen atom, an alkyl group having 1 to 8 carbon atoms, a lower alkoxycarbonyl group or a substituted or unsubstituted phenyl group or taken together represent a tetramethylene group corresponding to a fused cyclohexane ring or a butadienylene group which is unsubstituted or substituted with a halogen atom, a lower alkoxy group, a lower alkoxycarbonyl group or an alkyl group having 1 to 3 carbon atoms corresponding to a fused benzene ring; $R_3$, $R_4$, $R_5$ and $R_6$ each independently represent a hydrogen atom, a hydroxyl group, a lower alkoxy group, an alkyl group having 1 to 3 carbon atoms or a halogen atom; A represents a linking group having 2 to 4 chain members; B represents a linking group having 2 to 5 chain members; and Q represents a carboxyl group, a lower alkoxy group, a hydroxyl group, an alkoxycarbonyl group having 2 to 6 carbon atoms or a 5-tetrazolyl group.

DETAILED DESCRIPTION OF THE INVENTION

In the above formula (I), the alkyl group having 1 to 3 carbon atoms may include methyl, ethyl, propyl and isopropyl. The alkyl group having 1 to 8 carbon atoms may include, in addition to the alkyl groups having 1 to 3 carbon atoms as mentioned above, straight and branched aliphatic groups having 4 to 8 carbon atoms such as butyl, isobutyl, sec-butyl, t-butyl, amyl, isoamyl, sec-amyl, sec-isoamyl (1,2-dimethylpropyl), t-amyl (1,1-dimethylpropyl), hexyl, isohexyl (4-methylpentyl), sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, heptyl, isoheptyl (5-methylhexyl), 2,2-dimethylpentyl, 3,3-dimethylpentyl, 4,4-dimethylpentyl, 1,2dimethylpentyl, 1,3-dimethylpentyl, 1,4-dimethylpentyl, 1,2,3-trimethylbutyl, 1,1,2-trimethylbutyl, 1,1,3-trimethylbutyl, octyl, isooctyl (6-methylheptyl), sec-octyl (1-methylheptyl) and t-octyl (1,1,3,3-tetramethylbutyl) group, etc. The lower alkoxy group may include straight and branched alkoxy groups having 1 to 3 carbon atoms such as methoxy, ethoxy, propoxy and isopropoxy group, etc. The lower alkoxy carbonyl group may include straight and branched alkoxycarbonyl groups having 2 to 4 carbon atoms such as methoxycarbonyl, ethoxycarbonyl, propoxycarbonyl and isopropoxycarbonyl group. The alkoxy carbonyl group having 2 to 6 carbon atoms may include, in addition to the lower alkoxycarbonyl group as mentioned above, alkoxycarbonyl groups having 5 to 6 carbon atoms such as butoxycarbonyl group and amyloxycarbonyl group and isomer-substituted groups of these. Examples of the halogen atom may include fluorine atom, chlorine atom, bromine atom and iodine atom. As the substituent on the substituted phenyl group in the definition of $R_1$ and $R_2$, there may be employed, for example, the alkyl group having 1 to 3 carbon atoms, lower alkoxy group, lower alkoxycarbonyl group and halogen atom as mentioned above. As the linking group in the definition of A, any group having 2 to 4 atoms as the chain member constituting the linking group may be used, but it should particularly preferably contain carbon atom, oxygen atom, and nitrogen atom. Examples of such a linking group may include —CH=CH—, —CH$_2$CH$_2$—, —OCH$_2$—, —NHCH$_2$—, —CONH—, —CH=CH—CONH—, —CH$_2$OCH$_2$—, more preferably —CH=CH—, —CH$_2$CH$_2$—. As the linking group in the definition of B, any group having 2 to 5 atoms in the chain group constituting the linking group may be used, but it should particularly preferably contain carbon atom, oxygen atom and nitrogen atom. Examples of such a linking group may include —(CH$_2$)$_n$—CONH— (wherein n represents an integer of 0–3), —(CH$_2$)$_n$—NH— (wherein n represents an integer of 1–4), —(CH$_2$)$_n$—O— (wherein n represents an integer of 1–4), —(CH$_2$)$_n$— (wherein n represents an integer of 2–5),

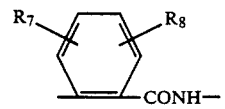

wherein $R_7$ and $R_8$ each independently represent a hydrogen atom or an alkyl group having 1 to 3 carbon atoms as defined above),

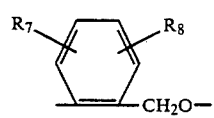

(wherein $R_7$ and $R_8$ have the same meanings as defined above),

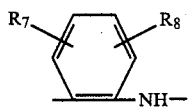

(wherein $R_7$ and $R_8$ have the same meanings as defined above),

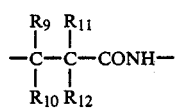

(wherein $R_9$, $R_{10}$, $R_{11}$ and $R_{12}$ each independently represent a hydrogen atom, a phenyl group or an alkyl group having 1 to 6 carbon atoms),

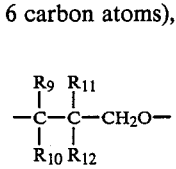

(wherein $R_9$, $R_{10}$, $R_{11}$ and $R_{12}$ have the same meanings as defined above),

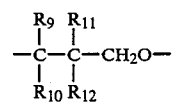

(wherein $R_9$ and $R_{11}$ have the same meanings as defined above),

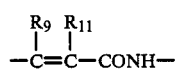

(wherein $R_{10}$ and $R_{12}$ have the same meanings as defined above),

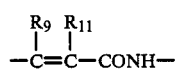

(wherein $R_{10}$ and $R_{12}$ have the same meanings as defined above),

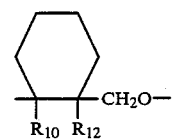

(wherein $R_{10}$ and $R_{12}$ have the same meanings as defined above),

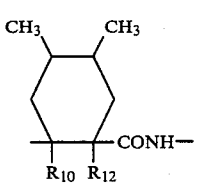

(wherein $R_{10}$ and $R_{12}$ have the same meanings as defined above),

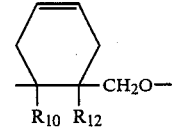

(wherein $R_{10}$ and $R_{12}$ have the same meanings as defined above),

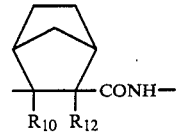

(wherein $R_{10}$ and $R_{12}$ have the same meanings as defined above),

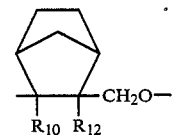

(wherein $R_{10}$ and $R_{12}$ have the same meanings as defined above),

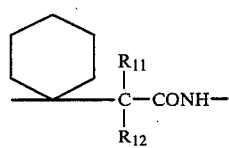

(wherein $R_{11}$ and $R_{12}$ have the same meanings as defined above), gen atom to the benzene ring can be synthesized according to the synthetic routes [A]–[C].

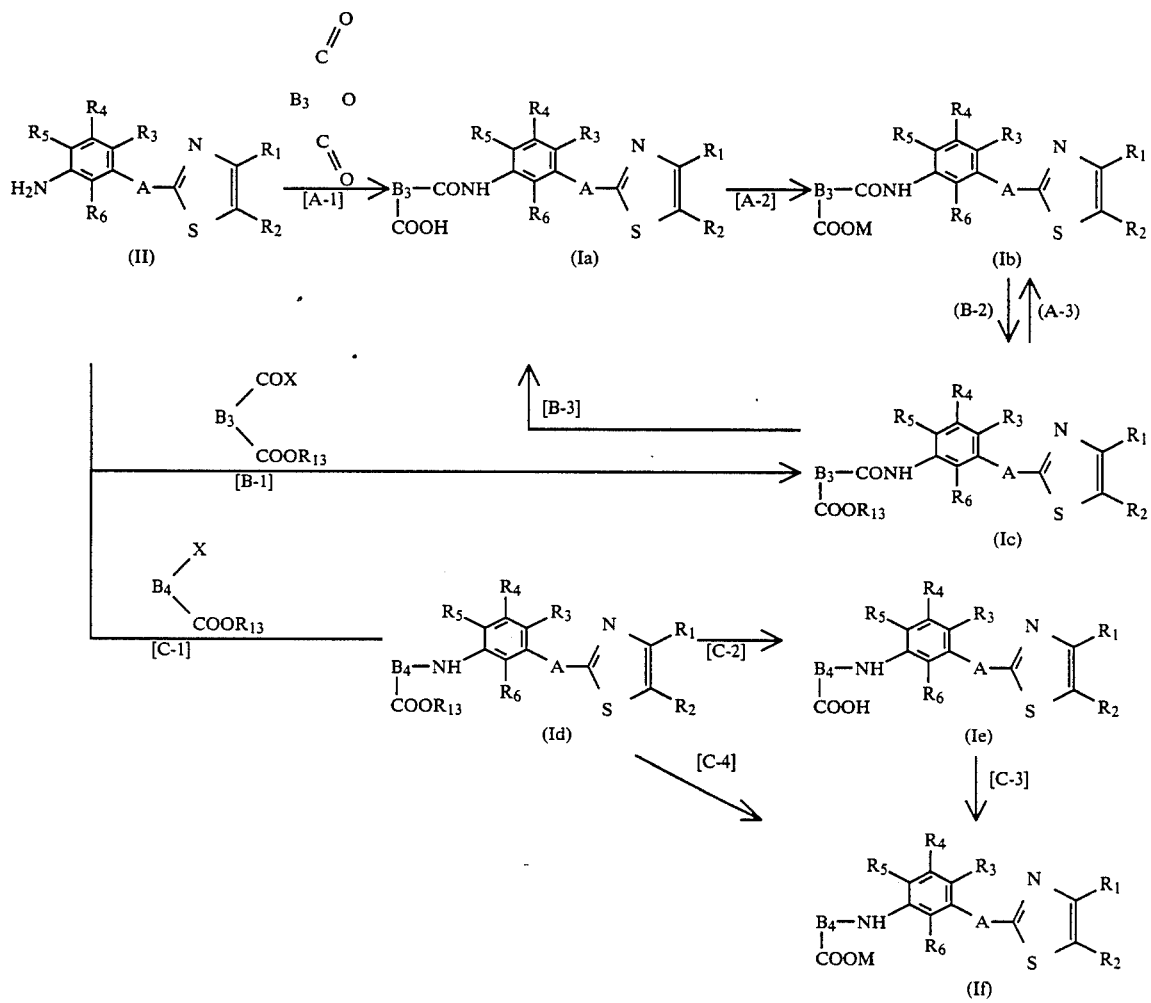

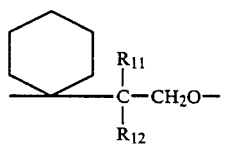

(wherein $R_{11}$ and $R_{12}$ have the same meanings as defined above), more preferably $$-\overset{\underset{\displaystyle R_{10}}{\displaystyle R_9}}{C}-\overset{\underset{\displaystyle R_{12}}{\displaystyle R_{11}}}{C}-CONH-$$

(wherein $R_{11}$ and $R_{12}$ each represent a hydrogen atom and $R_9$ and $R_{10}$ each independently represent an alkyl group having 1 to 6 carbon atoms).

The thiazole derivative of the present invention is not limited to a specific isomer, but includes all of geometric isomers, steric isomers, optical isomers and their mixtures such as racemic mixture.

The thiazole derivative of the present invention can be synthesized according to various methods.

For example, in the above formula (I), the compound wherein the linking group B is bonded through a nitro- In the synthetic routes, $R_1$, $R_2$, $R_3$, $R_4$, $R_5$, $R_6$ and A have the same meanings as defined above, $B_3$ represents a direct bond or a linking group having 1 to 3 chain members, $B_4$ represents a linking group having 1 to 4 chain members, M represents an alkali metal atom, X represents a halogen atom and $R_{13}$ represents an alkyl group having 1 to 5 carbon atoms.

The aniline derivative (II) used as the starting material can be synthesized according to the known method [Tetrahedron Letters, 25, 839 (1984)].

In the synthetic route [A], the aniline derivative (II) is allowed to react with 0.8 to 2 equal amounts of a cyclic acid anhydride to obtain the compound (Ia) (step [A-1]). As the reaction solvent, there may be employed aromatic hydrocarbons such as toluene, benzene, etc.; ether type solvent such as ethyl ether, dioxane, tetrahydrofuran, etc.; halogenated hydrocarbons such as chloroform, dichloromethane, etc. This reaction may be practiced at a temperature from under ice-cooling to the boiling point of the solvent, particularly preferably from room temperature to 60° C. The compound (Ia) can be converted to an alkali metal salt (Ib) by the reaction with a carbonate, a hydrogen carbonate or a hydroxide of the corresponding alkali metal in a hydrous alcoholic solvent (step [A-2]). Further, the compound (Ib) can be allowed to react with 1 to 3 equivalents of an alkylating agent such as an alkyl halide or an alkyl sulfonate, etc., in a non-protonic polar solvent such as dimethyl sulfoxide, dimethylformamide, hexamethylphosphoramide triamide, etc., at 0° to 100° C. to be alkylated and converted to a carboxylic acid ester (Ic) (step [A-3]).

In the synthetic route [B], the compound (II) can be acylated by the reaction with a carboxylic acid monoester monohalide in the presence of an organic base such as pyridine, triethylamine, etc., or an inorganic base such as potassium carbonate, sodium hydrogen carbonate, etc., at 0°–100° C. to synthesize the compound (Ic) (step [B-1]). As the reaction solvent, there may be used aromatic hydrocarbons, ether type solvents, halogenated hydrocarbons or non-protonic polar solvents. The compound (Ic) can be hydrolyzed in a conventional manner in a hydrous alcoholic solvent with an alkali metal type inorganic base such as sodium hydroxide, potassium carbonate, etc., to be readily converted to the compound (Ib) (step [B-2]). Also, after the above hydrolysis, the product can be treated with a mineral acid to obtain a free carboxylic acid (Ia) (step [B-3]).

In the synthetic route [C], the compound (II) can be allowed to react with a ω-halocarboxylic acid ester in the presence of an organic base such as triethylamine, pyridine, etc., in an aromatic hydrocarbon type, ether type or halogenated hydrocarbon type solvent at a temperature from 0° C. to the boiling point of the solvent to effect N-alkylation and result in synthesis of the compound (Id) (step [C-1]). The compound (Ie) can be synthesized according to the same method as in the step [B-3] (step [C-2]), and the compound (If) can be synthesized in the same manner as in the step [A-2] or the step [B-2] (step [C-3], step [C-4]).

In the above formula (I), the compound wherein the linking group B is bonded through an oxygen atom to the benzene ring can be synthesized according to the synthetic route [D] shown below.

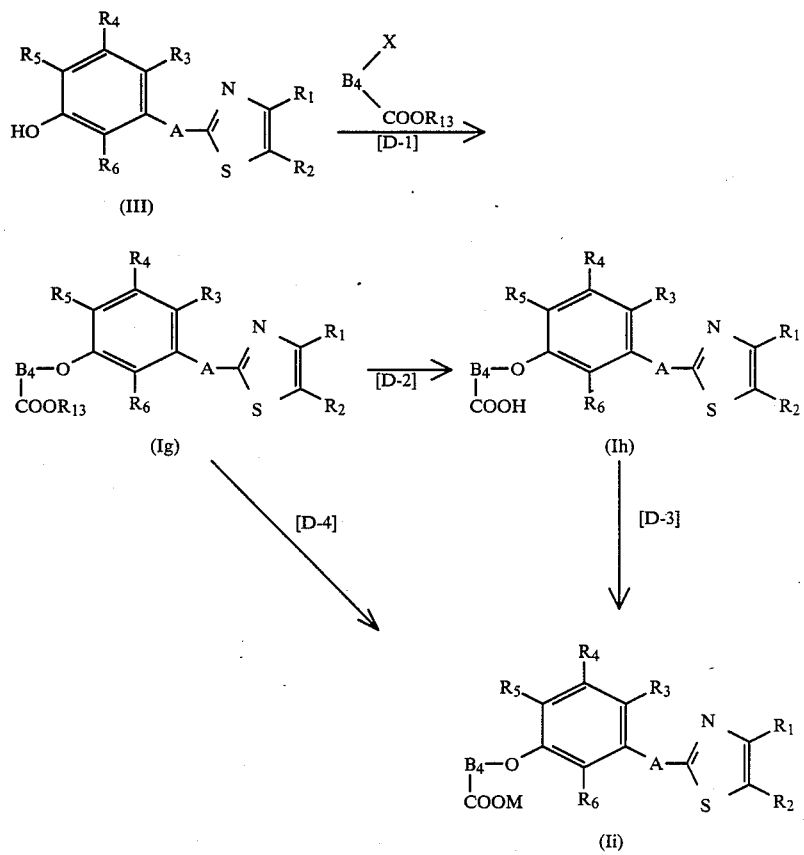

In the above synthetic route, $R_1$, $R_2$, $R_3$, $R_4$, $R_5$, $R_6$, $R_{13}$, A, $B_4$, M and X have the same meaning as defined above.

The phenol derivative (III) used as the starting material can be synthesized according to the known method [Journal of Medicinal Chemistry, 25, 1378 (1982)].

By O-alkylation of the compound (III) with a ω-halocarboxylic acid ester in a solvent of ketone type such as acetone, methyl ethyl ketone, etc., or alcohol type, in the presence of an inorganic base such as potassium carbonate, sodium hydrogen carbonate, etc., at a temperature from 0° C. to the boiling point of the solvent, the phenylether compound (Ig) can be synthesized (step [D-1]). The compound (Ih) can be obtained from the compound (Ig) similarly as in the step [B-2] (step [D-2]), and the compound (Ii) can be obtained from the compound (Ih) according to the same method as in the step [A-2] (step [D-3]), or from the compound (Ig) in the same manner as in the step [B-2] (step [D-4]).

In the above formula (I), the compound when the linking group A is a vinylene group can be synthesized according to the synthetic route [E] shown below.

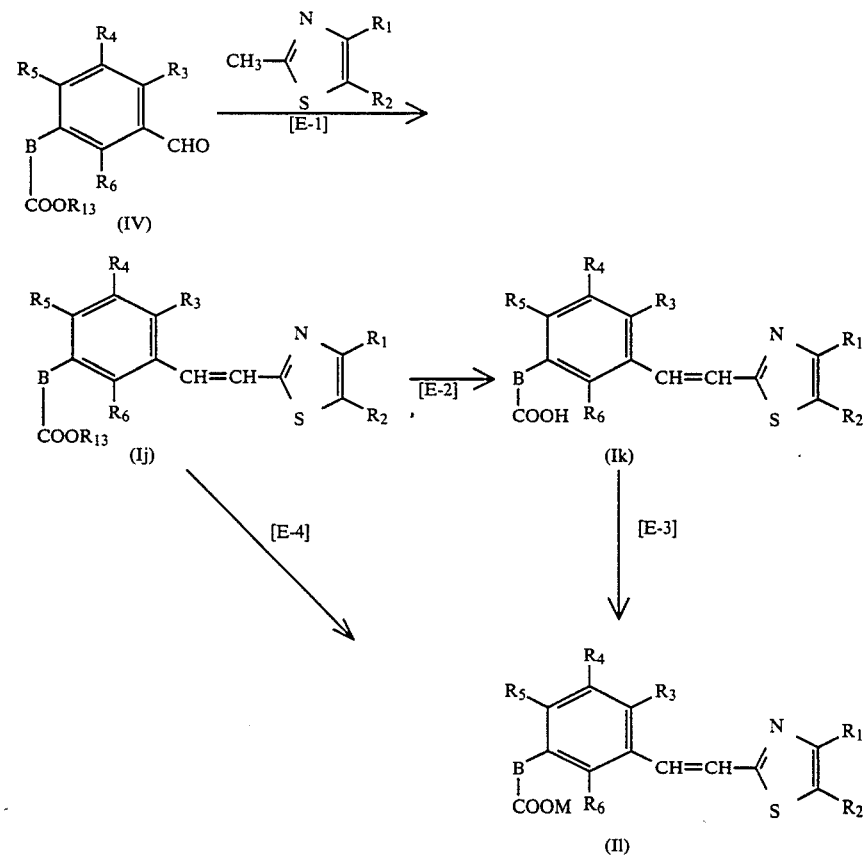

In the above synthetic route, $R_1$, $R_2$, $R_3$, $R_4$, $R_5$, $R_6$, $R_{13}$ B and M have the same meanings as defined above. The benzaldehyde derivative [IV] used as the starting material can be synthesized according to the known method [Journal of Medicinal Chemistry, 25, 1378 (1982)].

The compound (Ij) can be obtained according to the dehydrating condensation reaction by heating the benzaldehyde derivative (IV) and a 2-methylthiazole in acetic anhydride under nitrogen gas stream to 100°–200° C. (step [E-1]). Hydrolysis of the compound (Ij) in the same manner as in the step [B-3] gives the compound (Ik) (step [E-2]). From the compound (Ik), an alkali metal salt (Il) can be obtained in the same manner as in the step [A-2] (step [E-3]). The alkali metal salt (Il) can be obtained also by treating similarly the compound (Ij) as in the step [B-2] (step [E-4]).

The compound (I) of the present invention is characterized by having a marked leukotriene antagonistic action.

More specifically, when the antagonistic action to SRS was tested in vitro by use of an extirpated ileum of a guinea pig for the compound of the present invention, it has been found to have a selective antagonistic action for SRS even at an extremely low concentration. When further detailed $LTD_4$ antagonistic test was conducted by use of a guinea pig for some of the compounds of the present invention which have exhibited strong action in vitro test, it has been found that they can inhibit remarkably the asthmatic symptoms induced by $LTD_4$.

The leukotriene antagonist of the present invention contains the compound represented by the above formkla (I) or its pharmaceutically acceptable salt as the active ingredient together with a solid or liquid carrier or diluent for medicine, namely additives such as excepients, stabilizers, etc. When the compound (I) has a carboxylic group, preferable salts are non-toxic salts which are pharmaceutically acceptable such as alkali metal salts and alkaline earth metal salts such as sodium salts, potassium salts, magnesium salts, calcium salts or aluminum salts. It is similarly preferable to use adequate non-toxic amine salts such as ammonium salts, lower-alkylamine [e.g. triethylamine] salts, hydroxy lower-alkylamine [e.g. 2-hydroxyethylamine, bis-(2-hydroxyethyl)amine, tris(hydroxymethyl)aminomethane or N-methyl-D-glucamine] salts, cycloalkylamine [e.g. dicyclohexylamine] salts, benzylamine [e.g. N,N'-dibenzylethylenediamine] salts and dibenzylamine salts. In view of the basicity of the thiazole ring of the compound (I) of the present invention, preferable salts may include non-toxic salts such as hydrochlorides, methanesulfonates, hydrobromides, sulfates, phosphates, fumarates, succinates, etc. These salts are water-soluble and hence most preferable when used for injections. In said leukotriene antagonist, the proportion of the active ingredient to the carrier component in therapy may be variable between 1 wt. % to 90 wt. %. The leukotriene antagonist may be administered orally in the dosage form such as granules, fine particles, powders, tablets, hard capsules, soft capsules, syrup, emulsion, suspension or solution, or alternatively administered intravenously, intramuscularly or subcutaneously as injections. Also, it can be used as topical administration preparation to rectum, nose, eye, lung in the dosage form such as suppository, collunarium, eye drops or inhalent. Further, it can be used in the form of powder for injection which is to be formulated when used. It is possible to use an organic or inorganic, solid or liquid carrier or diluent for medicine suitable for oral, rectal, parenteral or local administration for preparation of the leukotriene antagonist of the present invention. Examples of the excepient to be used in preparation of a solid preparation may include lactose, sucrose, starch, talc, cellulose, dextrin, kaolin, calcium carbonate, etc. Liquid preparations for oral administration, namely, emulsion, syrup, suspension, solution, etc., contain inert diluents generally employed such as water or vegetable oils, etc. These preparations can contain auxiliary agents other than inert diluents such as humectants, suspension aids, sweeteners, aromatics, colorants or preservatives. It may also be formulated into a liquid preparation which is contained in capsules of absorbable substances such as gelatin. As the solvent or suspending agent to be used for production of preparations for parentheral administration, namely injections, suppositories, collunarium, eye drops, inhalent, etc., there may be employed, for example, water, propylene glycol, polyethylene glycol, benzyl alcohol, ethyl oleate, lecithin, etc. As the base to be used for suppository, there may be included, for example, cacao fat, emulsified cacao fat, laurine fat, Witepp sol, etc. The preparations can be prepared according to conventional methods.

The clinical dose, when used by oral administration, may be generally 0.01 to 1000 mg/day as the compound of the present invention for human adult, preferably 0.01 to 100 mg, but it is more preferable to increase or decrease suitably the dose depending on the age, condition of disease and symptoms. The above mentioned dose per day of the leukotriene antagonist may be administered once per day or in 2 or 3 divided doses per day at suitable intervals, or intermittently.

On the other hand, when used as an injection, it is preferable to administer continuously or intermittently 0.001 to 100 mg/administration as the compound of the present invention to human adult.

According to the present invention, a novel thiazole derivative having remarkable leukotriene antagonistic action can be provided. Said thiazole derivative is useful as the leukotriene antagonist for prophylaxis and therapy of various diseases in which leukotriene participates.

The present invention is described in more detail by referring to Synthesis examples, Examples and Test examples, but these are not intended to limit the scope of the present invention at all. In Synthesis examples and Examples, the symbols of "IR", "TLC", "NMR" and "MS" represent "infrared-absorption spectrum", "thin layer chromatography", "nuclear magnetic resonance spectrum" and "mass analysis", respectively, the proportion of the solvent written at the site of separation by chromatography indicating volume ratio, the solvent in the parenthesis of "TLC" indicating a developing solvent, "IR" being measured according to the KBr tablet method unless otherwise specifically noted, and the solvent in the parenthesis of "NMR" indicating the measurement solvent.

SYNTHESIS EXAMPLE 1

Synthesis of 4-isopropyl-2-methylthiazole

To a solution of 25 g of 3-methyl-2-butanone dissolved in 174 ml of methanol, 15.8 ml of bromine was added dropwise while temperature of the reaction mixture was maintained within the range of 0° to 5° C., and further the mixture was stirred at 10° C. for 1 hour. Then, 87 ml of water was added and the mixture was stirred at room temperature overnight. After completion of the reaction, the reaction mixture was extracted with ethyl ether, the extract was washed with 10% aqueous potassium carbonate solution and dried over calcium chloride, followed by evaporation of the solvent to give 53.2 g of a crude product of 1-bromo-3-methyl-4-butanone as colorless liquid. Further, without purification, 43.2 g of the above bromoketone was dissolved in 100 ml of ethanol and the solution was added at room temperature to a solution of 19.7 g of thioacetamide dissolved in 150 ml of ethanol. After the reaction was completed by refluxing for 2.5 hours, ethanol was evaporated under reduced pressure and the residue was ice-cooled to precipitate crystals. The crystals are washed with ethyl ether, poured into 250 ml of an aqueous saturated sodium hydrogen carbonate solution, free bases were extracted with n-hexane, followed by drying over anhydrous magnesium sulfate and concentration under reduced pressure to give 27.1 g (yield 73%) of the title compound as pale brown liquid.

IR (film): $\nu = 2950, 1510, 1450, 1165, 730$ cm$^{-1}$.
NMR (CDCl$_3$): $\delta = 1.30(6H,d), 2.68(3H,s), 3.07(1H,m), 6.67(1H,s)$.

SYNTHESIS EXAMPLE 2

Synthesis of 4-isopropyl-2-(trans-3-nitrostyryl) thiazole

To 11.3 ml of acetic anhydride were added 29.0 g of 3-nitrobenzaldehyde and 27.1 g of 4-isopropyl-2-methylthiazole and the reaction was carried out under nitrogen gas stream at 170° C. for 23 hours. After completion of the reaction, low boiling materials were evaporated under reduced pressure and the residue was recrystallized from ethyl ether-n-hexane to give 16.8 g (yield 32%) of the title compound as yellowish white crystals.

NMR (CDCl$_3$): $\delta = 1.34(6H,d), 3.12(1H,m), 6.86(1H,s), 7.2-8.4(6H,m)$.
IR: $\nu = 1625, 1590, 1435, 1305, 1210, 945, 770$ cm$^{-1}$.

SYNTHESIS EXAMPLE 3

Synthesis of 2-(3-nitrophenyl)methoxymethylbenzothiazole

A mixture of 1.60 g of 3-nitrobenzyl chloride, 1.3 g of 2-hydroxymethylbenzothiazole and 0.54 of potassium carbonate in 20 ml of acetone was stirred at room temperature for 1.5 hours and then refluxed for 30 minutes. After evaporation of acetone under reduced pressure, the residue was dissolved in ethyl acetate, washed with water and dried over magnesium sulfate, followed by evaporation of the solvent under reduced pressure. The residue was purified through a silica gel column chromatography by use of ethyl ether-n-hexane to obtain 1.7 g (yield 73%) of the title compound.

IR: $\nu = 1520, 1340, 1090, 800, 766, 725$ cm$^{-1}$.
NMR (CDCl$_3$): $\delta = 4.65(2H,s), 4.90(2H,s), 7.1-8.2 (8H,m)$.

SYNTHESIS EXAMPLE 4

Synthesis of 2-[2-(3-hydroxyphenyl)ethyl]benzothiazole

A mixture of 6.0 g of 2-(trans-3-hydroxystyryl) benzothiazole and 0.5 g of 5% palladium-carbon in 80 ml of ethanol was stirred under hydrogen gas stream under normal pressure at 50° to 60° C. for 3 hours. After completion of the reaction, the catalyst was filtered off and the filtrate was evaporated under reduced pressure to obtain 5.5 g (yield 92%) of the title compound as pale gray crystals.

IR: $\nu=3050, 1580, 1480, 1280, 760$ cm$^{-1}$.
m.p.: 129°–130° C.

SYNTHESIS EXAMPLE 5

Synthesis of 2-(trans-3-hydroxystyryl)-4ethyl-5-methylthiazole

An amount of 3.0 g of 2-(trans-3-aminostyryl)-4-ethyl-5-methylthiazole was added to 18 ml of 20% hydrochloric acid and to the mixture was added dropwise slowly 3 ml of an aqueous solution of 0.86 g of sodium nitrite while maintaining the inner temperature at 4° to 5° C. After the mixture was stirred at the above temperature for 1.5 hours, the reaction mixture was added into 50 ml of boiling water over 20 minutes. After the mixture was cooled to room temperature, the precipitates formed were collected by filtration, washed with aqueous saturated sodium hydrogen carbonate solution and with water, followed by drying under reduced pressure. The crude product was washed with toluene and dried under reduced pressure to obtain 2.1 g (yield 70%) of the title compound.

m.p.: 161°–162° C.
IR: $\nu=1620, 1598, 1575, 1215, 950, 778$ cm$^{-1}$.

SYNTHESIS EXAMPLE 6

(1) Synthesis of 2-(trans-3-hydroxystyryl)benzothiazole

A mixture of 25 g of 3-hydroxybenzaldehyde, 36.6 g of 2-methylbenzothiazole, 38.8 ml of acetic anhydride and 7.7 ml of formic acid was heated at 120° C. for 25 hours. The low boiling materials were evaporated together with toluene under reduced pressure, and the residue was added to 150 ml of methanol and refluxed with addition of 3 g of potassium carbonate for 1 hour. After cooled to room temperature, the mixture was filtered and filtrate was concentrated. The crude product formed was washed with methanol and ethyl ether and dried under reduced pressure to obtain 20.6 g (yield 40%) of the title compound.

m.p.: 210°–211° C.
IR: $\nu=1620, 1570, 1190, 1145, 935, 750$ cm$^{-1}$.

(2)

The operation similar to (1) was conducted to obtain 2-(trans-3-hydroxystyryl)-4-phenylthiazole (yield 21%).

m.p.: 150°–151° C.
IR: $\nu=3450, 1580, 1280, 950, 730$ cm$^{-1}$.

SYNTHESIS EXAMPLE 7

Synthesis of ethyl 5-(3-cyanophenyl-4pentenoate)

An amount of 0.66 g of 60% sodium hydride was added to 14 ml of anhydrous dimethyl sulfoxide and the mixture was heated under nitrogen gas stream to 75° to 80° C. to form dimsyl anions. After cooled to room temperature, the mixture was added to a solution of 6.3 g of 3-ethoxycarbonylpropyltriphenylphosphonium bromide in 20 ml of anhydrous dimethyl sulfoxide. The mixture was stirred at room temperature for 5 minutes and a solution of 1.5 g of 3-cyanobenzaldehyde in 4 ml of anhydrous dimethyl sulfoxide, followed by stirring at room temperature for 1.5 hours. After completion of the reaction, 5% hydrochloric acid was added to stop the reaction, and the reaction mixture was extracted with toluene. After evaporation of the solvent under reduced pressure, the residue was purified through silica gel column chromatography by use of ethyl ether-n-hexane to obtain 0.94 g (yield 36%) of the title compound as colorless oily product.

IR (film): $\nu=1725, 1245, 1180, 1150, 960, 785$ cm$^{-1}$.
NMR (CCl$_4$): $\delta=1.25(3H,t), 2.2–2.8(4H,m), 4.09(2H,q), 6.2–6.6(2H,m), 7.3–7.7(4H,m)$.

SYNTHESIS EXAMPLE 8

Synthesis of ethyl 5-(3-formylphenyl)pentanoate

An amount of 660 mg of ethyl 5-(3-cyanophenyl)-4-pentenoate and 60 mg of 5% palladium-carbon were added into 6 ml of ethanol and catalytic reduction was carried out under hydrogen gas stream at room temperature for 18 hours. After the catalyst was filtered off, the filtrate was evaporated under reduced pressure and 600 mg of the crude product was used for the subsequent reaction.

Into a suspension of 986 mg of anhydrous stannous chloride in anhydrous ethyl ether was introduced hydrogen chloride gas for 2 minutes to provide a uniform solution. Next, 600 mg of the above saturated carboxylic acid ester dissolved in 4 ml of ethyl ether was added and hydrogen chloride gas was introduced again for 1 minute, followed by stirring at room temperature for 5 hours. Subsequently, each 5 ml of ethyl ether and water was added and after stirred at room temperature for 1 hour, the organic layer was extracted with toluene. After drying over magnesium sulfate, the solvent was evaporated under reduced pressure and the residue was purified through silica gel column chromatography by use of ethyl ether-n-hexane to give 460 mg (yield 68%) of the title compound as colorless oily product.

IR (film): $\nu=1725, 1690, 1440, 1365, 1235, 1180, 1020, 790$ cm$^{-1}$.
NMR (CCl$_4$): $\delta=1.20(3H,t), 1.4–1.9(4H,m), 2.0–2.9(4H,m), 4.5(2H,q), 7.2–7.8(4H,m), 9.88(1H,s)$.

SYNTHESIS EXAMPLE 9

Synthesis of 2-[trans-3-(3-cyanopropylamino)styryl]benzothiazole

To 50 ml of toluene were added 2.02 g of triethylamine and 5.04 g of 2-(trans-3-aminostyryl)benzothiazole at room temperature, and then 2.96 g of 4-bromobutyronitrile was added to carry out the reaction at 110° C. for 7 hours. After completion of the reaction, the reaction mixture was extracted with ethyl acetate. After evaporation of the solvent under reduced pressure, the residue was purified through silica gel column chromatography by use of ethyl acetate-ethyl ether-n-hexane (2:5:5) to give 2.55 g (yield 40%) of the title compound as colorless oily product.

m.p.: 97°–98° C.
IR: $\nu=3400, 2250, 1600, 950, 760$ cm$^{-1}$.

SYNTHESIS EXAMPLE 10

Synthesis of 4-isopropyl-2-(trans-3-aminostyryl)thiazole

To a solution of 16.8 g of 4-isopropyl-2-(trans-3-nitrostyryl)thiazole dissolved in 60 ml of ethanol was added a solution of 48.4 g of stannous chloride dihydrate in 60 ml of ethanol and the mixture was refluxed for 1.5 hours. After the reaction mixture was cooled to room temperature, the mixture was adjusted to pH 13 with addition of 30% aqueous sodium hydroxide solution and then the basic portion was extracted with the use of ethyl acetate and dried over magnesium sulfate, followed by evaporation of the solvent under reduced pressure. The solid residue formed was recrystallized from ethyl ether-n-hexane to obtain 7.1 g (yield 47%) of the pale yellowish white title compound.

m.p.: 62°–63° C.

IR: $\nu = 3430, 3300, 1600, 1580, 960, 780, 740$ cm$^{-1}$.

NMR (CDCl$_3$): $\delta = 1.32(6H,d)$, 2.90–3.4(1H,m), 3.70(2H,s), 6.5–7.3(7H,m).

SYNTHESIS EXAMPLE 11

Synthesis of various thiazole derivatives

By carrying out the treatment similarly as in Synthesis example 10, various thiazole derivatives shown as Nos. 1–32 and 36–38 in Table 1 were obtained.

SYNTHESIS EXAMPLE 12

Synthesis of 2-[2-(3-aminophenyl)ethyl]-4-ethyl-5-methylthiazole

An amount of 1.0 g of 2-(3-aminostyryl)-4-ethyl-5-methylthiazole and 200 mg of 5% palladium-carbon were added to 20 ml of ethanol and catalytic reduction was carried out in a hydrogen gas atmosphere at room temperature and normal pressure for 12 hours. After the reaction mixture was filtered, the solvent was evaporated under reduced pressure to give 0.90 g (yield 90%) of the title compound as pale yellow crystals.

m.p.: 64°–65° C.

IR: $\nu = 3410, 1590, 1300, 1120, 950, 760$ cm$^{-1}$.

SYNTHESIS EXAMPLE 13

Synthesis of various 2-[2-(3-aminophenyl)ethyl]thiazoles

By carrying out the treatment similarly as in Synthesis example 12, various 2-[2-(3-aminophenyl)ethyl]thiazoles shown as Nos. 34 and 35 in Table 1 were obtained.

SYNTHESIS EXAMPLE 14

Synthesis of 2-(trans-3-amino-4-hydroxystyryl)benzothiazole

To a solution of 282 mg of 2-(trans-3-amino-4-methoxystyryl)benzothiazole dissolved in 30 ml of dichloromethane was added 380 mg of phosphorous tribromide at 70° C., and the mixture was gradually returned to room temperature and stirred overnight. After an aqueous saturated sodium hydrogen carbonate solution was added to the reaction mixture to make it weakly alkaline, the mixture was extracted with ethyl acetate. The extract was dried over anhydrous magnesium sulfate and the solvent was evaporated under reduced pressure to give 260 mg (yield 97%) of the title compound.

m.p.: 192°–193° C.

IR: $\nu = 3400, 1590, 1510, 1290, 800, 760$ cm$^{-1}$.

SYNTHESIS EXAMPLE 15

Synthesis of 2-(trans-3-amino-6-hydroxystyryl)benzothiazole

By carrying out the treatment similarly as in Synthesis example 14, the title compound shown as No. 33 in Table 1 was obtained.

SYNTHESIS EXAMPLE 16

Synthesis of 2-(trans-3-aminostyryl)-5-methoxycarbonylbenzothiazole

To a solvent mixture of 50 ml of dioxane and 30 ml of methanol, 2.0 g of 5-methoxycarbonyl-2-(trans-3-nitrostyryl)benzothiazole was added and, under vigorous stirring, a solution of 0.37 g of calcium chloride in 55 ml of water and 9.8 g of zinc powder were added, followed by refluxing for 2 hours. After cooled to room temperature, the reaction mixture was filtered and the filtrate was concentrated under reduced pressure, and the solid residue formed was washed with toluene to give 1.4 g (yield 77%) of the title compound.

m.p.: 165°–167° C.

IR: $\nu = 1710, 1630, 1305, 1100, 755$ cm$^{-1}$.

EXAMPLE 1

Synthesis of 2-[trans-3-(cis-3-carboxypropenamide)styryl]benzothiazole (compound No. 1)

To 8 ml of toluene were added 158 mg of 2-(trans-3-aminostyryl)benzothiazole and 71 mg of maleic anhydride, and the mixture was heated at 80° C. for 1 hour. After cooled to room temperature, the crystals formed were collected by filtration and recrystallized from ethanol to give 194 mg (yield 88%) of the yellowish white title compound.

m.p.: 190°–191° C.

IR: $\nu = 1700, 1625, 1550, 1490, 1405, 953$ cm$^{-1}$.

EXAMPLE 2

Synthesis of various anilide carboxylic acids

By carrying out the treatment similarly as in Example 1, the title compounds shown as compounds Nos. 2–165 and 445–448 in Table 2 were obtained.

EXAMPLE 3

Synthesis of 2-(trans-3-oxalylaminostyryl)-4-phenylthiazole (compound No. 166)

To a suspension of 1.0 g of 2-(trans-3ethyloxalylaminostyryl)-4-phenylthiazole in 40 ml of dioxane was added, under vigorous stirring, 1 ml of an aqueous 20% potassium hydroxide solution, and hydrolysis was carried out at room temperature for 1 hour. To the reaction mixture was added 20% hydrochloric acid to adjust the pH to 1–2, and the yellow precipitates formed were collected by filtration and washed with ethanol and chloroform, followed by drying under reduced pressure to give 870 mg (yield 94%) of the title compound.

m.p.: 291°–292° C.

IR: $\nu = 1715, 1685, 1590, 1520, 1300, 1180, 740$ cm$^{-1}$.

EXAMPLE 4

Synthesis of various anilidecarboxylic acids

By carrying out the treatment similarly as in Example 3, the title compounds shown as compounds Nos. 167–169 in Table 2 were obtained.

EXAMPLE 5

Synthesis of 2-[trans-3-(3-carboxypropylamino)styryl]-4-propylthiazole (compound No. 170)

To 20 ml of toluene were added 732 mg of 2-(trans-3-aminostyryl)-4-propylthiazole, 1170 mg of ethyl 4-bromobutyrate and 606 mg of triethylamine, and the reaction was carried out at 100° C. for 21 hours. After the reaction mixture was cooled to room temperature, 10 ml of ethanol and 10 ml of an aqueous 5% sodium hydroxide solution were added and the mixture was stirred at room temperature for 1.5 hours to effect hydrolysis of the ester. After completion of the reaction, ethanol was evaporated under reduced pressure and the residue was adjusted to pH 1-2 with addition of 10% hydrochloric acid, followed by extraction with ethyl ether. After drying over anhydrous magnesium sulfate, the solvent was evaporated and the solid formed was recrystallized from ethyl ether to give 629 mg (yield 64%) of the title compound.

m.p.: 115°–116° C.
IR: $\nu = 1705, 1595, 1480, 1190, 940, 740$ cm$^{-1}$.

EXAMPLE 6

Synthesis of various anilinocarboxylic acid

By carrying out the treatment similarly as in Example 5, the title compounds shown as compounds Nos. 171–182 in Table 2 were obtained.

EXAMPLE 7

Synthesis of 2-(trans-3-ethyloxalylaminostyryl)-4-phenylthiazole (compound No. 183)

To 30 ml of toluene were added 0.7 g of pyridine and 2.0 g of 2-(trans-3-aminostyryl)-4-phenylthiazole and a solution of 1.1 g of ethyloxalyl chloride in 5 ml of toluene was added dropwise at 0° C. under stirring, followed by heating at 50° C. for 1.5 hours. The reaction mixture was poured into ice-cold water and crystals formed were collected by filtration and dried, followed by recrystallization from chloroform to give 2.5 g (yield 90%) of the title compound.

m.p.: 193°–194° C.
IR: $\nu = 3325, 1715, 1700, 1300, 730$ cm$^{-1}$.

EXAMPLE 8

Synthesis of various anilidecarboxylic acid esters

By carrying out the treatment similarly as in Example 7, the title compounds shown as compounds Nos. 184–188 in Table 2 were obtained.

EXAMPLE 9

Synthesis of 2-[trans-3-(cis-3-isoamyloxycarbonylpropenamide)styryl]benzothiazole (compound No. 189)

To 6 ml of hexamethylphosphoric triamide were added 1.0 g of sodium salt of 2-[trans-3-(cis-3-carboxypropenamide)styryl]benzothiazole and 2.13 g of isoamyliodide, and the mixture was stirred at room temperature for 4 hours. The reaction mixture was extracted with toluene in a conventional manner, the extract was dried over anhydrous magnesium sulfate and the solvent was evaporated under reduced pressure, followed by recrystallization of the residue from ethyl ether-toluene to give 616 mg (yield 55%) of the title compound.

m.p.: 82°–83° C.
IR: $\nu = 3400, 1720, 1660, 1580, 1440, 1200, 755$ cm$^{-1}$.

EXAMPLE 10

Synthesis of various anilidecarboxylic acid esters

By carrying out the treatment similarly as in Example 9, the title compounds shown as compounds Nos. 190–195 in Table 2 were obtained.

EXAMPLE 11

Synthesis of 2-[trans-3-(4-ethoxycarbonyl)butylstyryl]benzothiazole (compound No. 196)

A mixture of 460 mg of ethyl 5-(3-formylphenyl)pentanoate, 322 mg of 2-methylbenzothiazole and 0.11 ml of acetic anhydride was heated under nitrogen gas stream to 170° C. for 30 hours. The reaction mixture was directly purified through silica gel column chromatography by use of ethyl ether-n-hexane to obtain 320 mg (yield 45%) of the title compound as brown oily product.

IR: $\nu = 1720, 1620, 1485, 1180, 950, 750$ cm$^{-1}$.
NMR (CCl$_4$): $\delta = 1.25(3H,t), 1.35$–$2.05(4H,m), 2.01$–$2.85(4H,m), 4.07(2H,q), 7.05$–$8.10(10H,m)$.

EXAMPLE 12

Synthesis of various 2-(trans-3-alkoxycarbonylalkylenestyryl)benzothiazoles

By carrying out the treatment similarly as in Example 11, the title compounds shown as compounds Nos. 197 and 198 in Table 2 were obtained.

EXAMPLE 13

Synthesis of 2-[trans-3-(3-ethoxycarbonylpropyl)aminostyryl]benzothiazole (compound No. 199)

To 10 ml of toluene were added 1.0 g of 2-(trans-3-aminostyryl)benzothiazole, 0.78 g of ethyl 4-bromobutyrate and 0.4 g of triethylamine, and the mixture was stirred at 100° C. for 20 hours. After cooled to room temperature, the mixture was extracted with toluene, dried over anhydrous magnesium sulfate and then the solvent was evaporated under reduced pressure. The residue was purified through silica gel column chromatography by use of ethyl acetate-n-hexane to obtain 951 mg of the title compound (yield 66%).

m.p.: 68°–69° C.
NMR (CDCl$_3$): $\delta = 1.25(3H,t), 2.0(2H,m), 2.35(2H,t), 3.22(2H,t), 4.23(2H,q), 6.45$–$8.10(10H,m)$.

EXAMPLE 14

Synthesis of various anilinocarboxylic acid esters

By carrying out the treatment similarly as in Example 13, the title compounds shown as compounds Nos. 200–205 in Table 2 were obtained.

EXAMPLE 15

Synthesis of 2-(trans-3-ethoxycarbonylmethoxystyryl)benzothiazole (compound No. 206)

To 30 ml of acetone were added 200 mg of 2-(trans-3-hydroxystyryl)benzothiazole, 0.11 ml of ethyl bromoacetate and 131 mg of potassium carbonate, and the mixture was refluxed for 4 hours. After cooled to room temperature, the mixture was extracted with ethyl ether, dried over anhydrous magnesium sulfate and then the solvent was evaporated under reduced pressure. After the crude crystals of the residue were washed with ethyl ether and n-hexane, they were dried under reduced pressure to give 207 ml (yield 77%) of the title compound.
m.p.: 150°–151° C.
IR: $\nu = 1720, 1585, 1260, 1190, 1025, 950, 755$ cm$^{-1}$.

EXAMPLE 16

Synthesis of various alkoxycarbonylalkylphenylethers

By carrying out the treatment similarly as in Example 15, the title compounds shown as compounds Nos. 207–212 and 431–433 in Table 2 were obtained.

EXAMPLE 17

Synthesis of 2-[trans-3-(cis-3-carboxypropenamide) styryl]benzothiazole sodium salt (compound No. 213)

To 350 ml of methanol was added 17.3 g of 2-[trans-3-(cis-3-carboxypropenamide)styryl]benzothiazole and then a solution of 4.1 g of sodium hydrogen carbonate in 75 ml of water, followed by refluxing for 1 hour. The solvent was evaporated under reduced pressure, and the crude crystals of the residue were washed with ethanol and ethyl ether, followed by drying under reduced pressure to give 18.9 g (yield: quantitative) of the title compound.
m.p.: 256°–258° C.
IR: $\nu = 1650, 1625, 1560, 1490, 855, 750$ cm$^{-1}$.

EXAMPLE 18

Synthesis of sodium salts of various carboxylic acids having thiazole groups

By carrying out the treatment similarly as in Example 17, the title compounds shown as compounds Nos. 214–395 and 434–436 in Table 2 were obtained.

EXAMPLE 19

Synthesis of 2-[trans-3-(3-carboxypropyl)aminostyryl]benzothiazole sodium salt (compound No. 396)

To 8 ml of ethanol were added 1.16 g of 2-[trans-3-(3-ethoxycarbonylpropyl)aminostyryl]benzothiazole and 5 ml of 5% aqueous sodium hydroxide solution, and the mixture was stirred at 60° C. for 1.5 hours. After evaporation of the solvent together with toluene under reduced pressure, the residue was diluted with ethanol and heated to 50° C. After cooled to room temperature, the crystals formed were collected by filtration and washed with ethanol-ethyl ether, followed by drying under reduced pressure to give 1.11 g (yield 97%) of the title compound.
m.p.: 239°–240° C.
IR: $\nu = 1360, 1570, 1410, 940, 760$ cm$^{-1}$.

EXAMPLE 20

Synthesis of sodium salts of various carboxylic acids having thiazole groups

By carrying out the treatment similarly as in Example 19, the title compound shown as compounds Nos. 397–413 in Table 2 were obtained.

EXAMPLE 21

Synthesis of 2-[trans-3-(cis-2-carboxycyclohexanoyl)aminostyryl]-benzothiazole N-methyl-D-glucamine salt (compound No. 414)

Into a solvent mixture of 6 ml of methanol and 1 ml of water were added 96 mg of N-methyl-D-glucamine and 200 mg of 2-[trans-3-(cis-2-carboxycyclohexanoyl)aminostyryl]benzothiazole and the mixture was stirred at room temperature for 30 minutes. After evaporation of the solvent under reduced pressure, the crude crystals formed were recrystallized from ethanol-ethyl ether to obtain 215 mg (yield 73%) of the title compound.
m.p.: 113°–115° C., 245°–246° C.
IR: $\nu = 1680, 1540, 1410, 1080, 750$ cm$^{-1}$.

EXAMPLE 22

Synthesis of salts with organic bases of various carboxylic acids having thiazole groups By carrying out the treatment similarly as in Example 21, the title compounds shown as compounds Nos. 415–421 in Table 2 were obtained. In Table 2, the following abbreviations were used.
NMG: N-methyl-D-glucamine,
Tris: tris(hydroxymethyl)aminomethane.

EXAMPLE 23

Synthesis of 2-[trans-3-(4-hydroxybutanoylamino) styryl]benzothiazole (compound No. 422)

A solution of 1.0 g of 2-(trans-3-aminostyryl)benzothiazole dissolved in 15 ml of anhydrous tetrahydrofuran was cooled to −78° C. and 2.8 ml of a n-hexane solution (1.55M) of n-butyl lithium was added dropwise in a nitrogen gas atmosphere. After a mixture was stirred at the same temperature for 25 minutes, 375 mg of γ-butyrolactone was injected, followed by stirring for 1 hour. After completion of the reaction, the mixture was extracted with ethyl acetate, dried over magnesium sulfate and the solvent was evaporated under reduced pressure. The crude crystals obtained were washed with ethyl ether and dried to obtain 160 mg (yield 12%) of the title compound.
m.p.: 191°–192° C.
IR: $\nu = 3400, 1640, 1580, 1530, 1420, 1050, 940, 755$ cm$^{-1}$.

EXAMPLE 24

Synthesis of 2-[trans-3-(4-hydroxybutoxy)styryl]benzothiazole (compound No. 423)

To 40 ml of ethyl ether was added 1.0 g of 2-[trans-3-(3-ethoxycarbonylpropoxy)styryl]benzothiazole, and 114 mg of lithium aluminum hydride was added under ice-cooling. After the mixture was stirred at the same temperature for 30 minutes, then at room temperature for 40 minutes, 114 μl of water, 114 μl of 15% aqueous sodium hydroxide and 340 μl of water were successively added slowly to decompose the aluminum complex, followed by extraction with toluene. After drying over anhydrous magnesium sklfate, the solvent was evaporated under reduced pressure and the crude crystals formed were washed with ethyl ether under ice-cooling, followed by drying under reduced pressure to give 570 mg (yield 64%) of the title compound.
m.p.: 88°–90° C.

IR: $\nu = 3280$, 1590, 1570, 1285, 950, 760 cm$^{-1}$.

EXAMPLE 25

Synthesis of
2-[trans-3-(3-(5-tetrazolyl)propylamino)styryl]benzothiazole (compound No. 424)

To 5 ml of dimethylformamide were added 390 mg of sodium azide and 638 mg of 2-[trans-3-(3-cyanopropylamino)styryl]benzothiazole, and the mixture was heated to 120° C. for 7 hours. After cooled to room temperature, the mixture was extracted with ethyl acetate, dried over anhydrous magnesium sulfate and the solvent was evaporation under reduced pressure. The concentrate was purified through silica gel column chromatography by use of ethyl acetate to obtain 250 mg (yield 35%) of the title compound.

m.p.: 168°–169° C.
IR: $\nu = 1625$, 1595, 1460, 1430, 950, 760 cm$^{-1}$.

EXAMPLE 26

Synthesis of
2-[trans-3-(2-carboxyanilino)styryl]benzothiazole (compound No. 425)

To 10 ml of isoamyl alcohol were added 504 mg of 2-(trans-3-aminostyryl)benzothiazole, 311 mg of 2-chlorobenzoic acid, 290 mg of potassium carbonate, 1 mg of iodine and 15 mg of copper powder, and the mixture was refluxed for 6 hours. The solvent was evaporated under reduced pressure and the residue was extracted with ethyl acetate. The crude product after evaporation of the solvent was purified through silica gel column chromatography by use of ethyl acetate-toluene to obtain 83 mg (yield 11%) of the title compound.

IR: $\nu = 1630$, 1570, 1380, 1285, 1200, 750 cm$^{-1}$.
m.p.: 146°–150° C.

EXAMPLE 27

Synthesis of 2-[trans-3-(2-carboxyethylamino) styryl]benzothiazole sodium salt (compound No. 426)

To 1 ml of acetonitrile were added 1.0 g of 2-(trans-3-aminostyryl)benzothiazole and 1 ml of β-propiolactone, and the mixture was refluxed for 1 hour. After evaporation of acetonitrile under reduced pressure, toluene and 10% hydrochloric acid were added to the residue. After the insolubles were filtered off, the filtrate was made alkaline with addition of 10% aqueous sodium hydroxide solution and the precipitates formed were collected by filtration. The crude product was recrystallized from methanol-ethyl acetate to obtain 224 mg (yield 16%) of the title compound.

m.p.: 250° C. (decomposed)
IR: $\nu = 1565$, 1405, 1005, 940, 750 cm$^{-1}$.

EXAMPLE 28

Synthesis of
2-[3-(2-carboxyethylamino)styryl]-4,5-dimethylthiazole sodium salt (compound No. 427)

An amount of 230 mg of 2-(trans-3-aminostyryl)-4,5-dimethylthiazole, 1 ml of methyl acrylate and two drops of acetic acid were added to 1.5 ml of toluene and the mixture was refluxed for 16 hours. The mixture was extracted in a conventional manner with ethyl acetate, the solvent was evaporated under reduced pressure and the residue was purified through silica gel column chromatography by use of ethyl acetate-n-hexane to obtain 160 mg of acrylate adduct. Next, 160 mg of the ester was dissolved in 5 ml of ethanol, and 2 ml of 5% aqueous sodium hydroxide was added to carry out hydrolysis by stirring at room temperature for 1 hour. The precipitates formed were collected by filtration, washed with water and then with ethyl ether, followed by drying under reduced pressure to obtain 90 mg (yield 28%) of the title compound.

m.p.: 120°–123° C.
IR: $\nu = 1595$, 1550, 1405, 945, 765 cm$^{-1}$.

EXAMPLE 29

Synthesis of 2-[trans-3-(2-carboxyethylamino) styryl]-4-phenylthiazole sodium salt (compound No. 428)

By carrying out the treatment similarly as in Example 28, 93 mg (yield 23%) of the title compound was obtained.

m.p.: 261°–263° C. (decomposed).
IR: $\nu = 1700$, 1590, 1440, 1220, 1195, 760 cm$^{-1}$.

EXAMPLE 30

Synthesis of
2-[trans-3-(2-carboxyethoxy)styryl]benzothiazole (compound No. 429)

To 3 ml of dimethylformamide were added 47 mg of 60% sodium hydride and 300 mg of 2-(trans-3-hydroxystyryl)benzothiazole, and the mixture was stirred at room temperature for 30 minutes. Then, 74 μl of β-propiolactone was added and the mixture was further stirred for 4.5 hours. The acidic portion was extracted in a conventional manner with chloroform, and after drying over anhydrous magnesium sulfate, the solvent was evaporated under reduced pressure and the crude crystals were washed with ethyl ether, followed by drying under reduced pressure to give 118 mg (yield 31%) of the title compound.

m.p.: 177°–178° C.
IR: $\nu = 1705$, 1590, 1440, 1215, 1195, 960, 760 cm$^{-1}$.

EXAMPLE 31

Synthesis of
2-[trans-3-(3-carboxy-3,3-dimethylpropyloxy)styryl]-4-isopropylthiazole (compound No. 430)

To a solution of 200 mg of 2-[trans-3-(3,3-dimethyl-3-ethoxycarbonylpropyloxy)styryl]-4-isopropylthiazole dissolved in 5 ml of ethanol were added 2 ml of 10% aqueous potassium hydroxide solution and three drops of 40% benzyltrimethylammonium hydroxide methanol solution, and the mixture was refluxed for 1 hour to effect hydrolysis of the ester. After completion of the reaction, ethanol was evaporated under reduced pressure and the residue was adjusted to pH 1–2 with addition of 10% hydrochloric acid and then extracted with ethyl ether. After drying of anhydrous magnesium sulfate, the solvent was evaporated and the solid formed was recrystallized from methanol to give 123 mg (yield 66%) of the title compound.

m.p.: 112°–113° C.
IR: $\nu = 1705$, 1285, 1160, 1100, 740 cm$^{-1}$.

EXAMPLE 32

Synthesis of various styrylcarboxylic acids

By carrying out the treatment similarly as in Example 31, the title compounds shown as compounds Nos. 438–444 in Table 2 were obtained.

EXAMPLE 33
Preparation of tablets

An amount of 1000 g of well pulverized 2-[trans-3-(cis-3-carboxypropenamide)styryl]benzothiazole sodium salt (compound No. 213), 5900 g of lactose, 2000 g crystalline cellulose, 1000 g of a low substitution degree hydroxypropyl cellulose and 100 g of magnesium stearate were well mixed and formed into plain tables according to the direct tableting method containing 10 mg of the above compound in 100 mg of one tablet. The plain tablet was applied with sugar coating or film coating to prepare sugar-coated tablet and film-coated tablet.

EXAMPLE 34
Preparation of capsules

An amount of 1000 g of well pulverized 2-[trans-3-(cis-3-carboxypropenamide)styryl]benzothiazole sodium salt (compound No. 213), 3000 g of corn starch, 6900 g of lactose, 1000 g of crystalline cellulose and 100 g of magnesium stearate were mixed to prepare capsules containing 10 mg of the above compound in 120 mg of one capsule.

EXAMPLE 35
Preparation of inhalent

An amount of 5 g of well pulverized 2-[trans-3-(cis-3-carboxypropenamide)styryl]benzothiazole sodium salt (compound No. 213), 10 g of a middle chain saturated fatty acid triglyceride and 0.2 g of sorbitane monooleate were well mixed, and each 15.2 mg of the mixture was weighed in 5 ml of an aluminum vessel for aerosol. Further, after 84.8 mg of Freon 12/114 (1:1 mixture) was filled per one vessel at low temperature, the vessel was equipped with a quantitative adaptor of 100 µl per 1 spray to prepare an inhalent of quantitative spray containing 5 mg of the above compound in 5 ml of one vessel.

EXAMPLE 36
SRS antagonistic action in vitro

The ileum end portion of a male Hartley-strain guinea pig weighing 200–450 g was extirpated and after washing its lumen, the ileum was mounted within 5 ml of a tissue bath containing a Tylord solution comprising the following components. The components are 136 mM NaCl, 2.7 mM KCl, 11.9 mM NaHCO$_3$, 1.05 mM MgCl$_2$, 1.8 mM CaCl$_2$, 0.4 mM NaH$_2$PO$_4$ and 5.6 mM glucose. The liquid temperature in the bath was maintained at 37° C., and aeration was effected with 95% oxygen/5% carbon dioxide. For removing shrinkage with hystamine and acetylcholine, $10^{-7}$ g/ml of mepylamin and $5\times 10^{-8}$ g/ml of atropin were added to the above buffer. Isotonic measurement was conducted by isotonic transducer (TD-112S, trade name, produced by Nippon Koden) tension replacement convertor and recorded by Recticoder (RTG-4124, trade name, produced by Nippon Koden) as the change in grams of tension. The ileum was loaded passively with 0.5 g of tension and the ileum shrinkage reaction to SRS extracted from guinea pig lung was obtained. The persistent shrinkage height by one unit of SRS (corresponding to 5 ng of hystamine) was used as control. Test drugs of various concentrations were added into the tissue bath, and the results of minimum effective concentration which is the concentration of the test drug attenuating shrinkage of control to 50% (IC$_{50}$) are shown in Table 2 and Table 3.

EXAMPLE 37
LTD$_4$ antagonistic action in vivo

For male Hartley-strain guinea pig weighing 350–500 g under urethane anesthesia, airway resistance was measured by use of a Harvard type respirator according to the method which is a modification of the Konzett-Roessler method, inhibition (%) by intraduodenal administration of the test drug against airway resistance increase by intraveneous administration of 0.1–1.0 µg/kg of LTD$_4$ was calculated to obtain the results shown in Table 2 and Table 4.

TEST EXAMPLE
Acute toxicity test

With 4 to 5 ddy-strain male mice of 6 weeks old as one group, the compound of the present invention was orally administered as a suspension in 1% tragacanth solution, and observation was conducted for 7 days and the number of dead mice was examined to obtain the results shown in Table 5.

TABLE 1-1

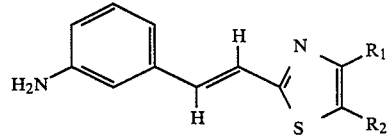

(IIa)

| No. | R$_1$ | R$_2$ | m.p. (°C.) |
|---|---|---|---|
| 1 | Me | Me | 148~149 |
| 2 | Et | " | 76~77 |
| 3 | " | H | 60~61 |
| 4 | CH$_3$(CH$_2$)$_2$— | " | 61~62 |
| 5 | CH$_3$(CH$_2$)$_3$— | " | 79~80 |
| 6 | CH$_3$(CH$_2$)$_4$— | " | 56~57 |
| 7 | CH$_3$(CH$_2$)$_5$— | " | 65~66 |
| 8 | CH$_3$(CH$_2$)$_6$— | " | 56~57 |
| 9 | CH$_3$(CH$_2$)$_7$— | " | 50~51 |
| 10 | CH$_3$(CH$_2$)$_2$— | Et | 58~59 |
| 11 | (CH$_3$)$_3$C— | H | 74~75 |
| 12 | Me | CH$_3$(CH$_2$)$_3$— | 58~59 |
| 13 | C$_6$H$_5$— | " | 138~139 |
| 14 | —COOEt | H | 93~94 |
| 15 | —(CH$_2$)$_4$— | | 156~157 |
| 16 | C$_6$H$_5$— | H | 137~139 |
| 17 | p-Cl —C$_6$H$_4$— | " | 177~178 |
| 18 | m-Me—C$_6$H$_4$— | " | 117~118 |
| 19 | p-EtOOC—C$_6$H$_4$— | " | 145~146 |
| 20 | p-Me—C$_6$H$_4$— | " | 156~157 |
| 21 | p-MeO—C$_6$H$_4$— | " | 141~142 |

TABLE 1-2

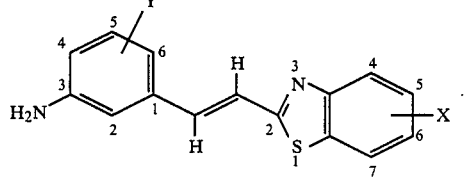

(IIb)

| No. | X | Y | m.p. (°C.) |
|---|---|---|---|
| 22 | H | H | 178~179 |
| 23 | 5-OMe | " | 143~144 |
| 24 | 5-Me | " | 150~151 |
| 25 | 5-Cl | " | 168~169 |
| 26 | 6-OMe | " | 158~160 |

TABLE 1-2-continued

(IIb)

| No. | X | Y | m.p. (°C.) |
|---|---|---|---|
| 27 | H | 2-Me | 118~120 |
| 28 | " | 6-OMe | 147~148 |
| 29 | " | 4-Cl | 174~176 |
| 30 | " | 6-Cl | 191~192 |
| 31 | " | 2-OH | 180~181 |
| 32 | " | 4-OMe | 155~156 |
| 33 | " | 6-OH | 234~236 |

TABLE 1-3

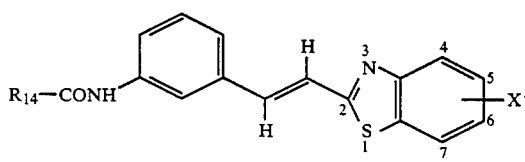

(IIc)

| No. | $R_1$ | $R_2$ | A | m.p. (°C.) |
|---|---|---|---|---|
| 34 |  |  | —(CH$_2$)$_2$— | 79~80 |
| 35 | (CH$_3$)$_2$CH— | H | " | —* |
| 36 | H | " | —CH$_2$OCH$_2$— | —** |
| 37 | " | " | —OCH$_2$— | 120~121 |
| 38 | " | " | —NHCH$_2$— | 102~103 |

*IR: 1600, 1450, 1160, 1100, 770, 730
**IR: 1620, 1460, 1310, 1090, 865, 760

TABLE 2-1

$R_{14}$—CONH—[structure with benzothiazole]—X

| Compound No. | $R_{14}$ | X | m.p. (°C.) | Physical property values | Anti-SRS action [minimum effective conc. (M)] | Airway resistance increase inhibition (%) |
|---|---|---|---|---|---|---|
| 2 | 2-COOH-phenyl | H | 193~4 | IR 1700, 1670, 1580, 1541, 1260, 750 | 5 × 10$^{-9}$ | |
| 3 | cis 2-COOH-cyclohexyl | " | 191~2 | IR 1705, 1660, 1542, 1488, 1080, 755 | 5 × 10$^{-8}$ | |
| 4 | cis 2-COOH-cyclohexenyl | " | 190~3 | IR 1705, 1660, 1600, 1540, 950, 760 | | |
| 5 | trans 2-COOH-cyclohexyl | " | 236~7 | IR 1715, 1650, 1530, 1080, 950, 750 | | |
| 6 | —(CH$_2$)$_2$COOH | " | 219~20 | IR 1690, 1540, 1315, 1210, 760 | | |
| 7 | —(CH$_2$)$_3$COOH | " | 227~30 | IR 1705, 1640, 1530, 1415, 1080, 765 | | |
| 8 | cis 4,5-diMe-2-COOH-cyclohexyl | " | 189~90 | IR 1690, 1670, 1410, 1200, 950, 750 | | |
| 9 | 4,5-diMe-2-COOH-phenyl | " | 198~202 | IR 1705, 1650, 1540, 1250, 780 | | |

TABLE 2-1-continued

Structure: R₁₄—CONH—(phenyl)—CH=CH—(benzothiazole with X substituent)

| Compound No. | R₁₄ | X | m.p. (°C.) | Physical property values | Anti-SRS action [minimum effective conc. (M)] | Airway resistance increase inhibition (%) |
|---|---|---|---|---|---|---|
| 10 | 1-ethylcyclohexyl-COOH | " | 168~171 | IR 1660, 1550, 1495, 1440, 1215, 955, 755 | | |
| 11 | Me₂C(COOH)- (with ethyl) | " | 177~8 | IR 1710, 1670, 1545, 1200, 755 | | |
| 12 | Et₂C(COOH)- | H | 160~1 | IR 1680, 1540, 1200, 950, 750 | | |
| 13 | PhCH(COOH)CH₂- | " | 191~2 | IR 1705, 1660, 1540, 1180, 755 | | |
| 14 | Me(CH₂)₂CH(Et)COOH | " | 169~70 | IR 1700, 1660, 1540, 1200, 950, 750 | | |
| 15 | Me(CH₂)₃CH(Et)COOH | " | 163~4 | IR 1710, 1660, 1540, 750 | | |
| 16 | Me(CH₂)₄CH(Et)COOH | " | 140~1 | IR 1700, 1655, 1540, 1310, 950, 750 | | |
| 17 | Me₂CHCH(Me)CH(Et)COOH | " | 191~2 | IR 1680, 1540, 1417, 1190, 753 | | |
| 18 | Me₂CHCH(Et)COOH (with Me) | " | 169~70 | IR 3210, 2950, 1680, 1540, 1080, 950, 750 | | |
| 19 | CH=CH-COOH (vinyl) | 5-Me | 211~2 | IR 1695, 1620, 1550, 1400, 850, 785 | | |
| 20 | 2-COOH-phenyl | " | 207~8 | IR 1705, 1650, 1260, 940, 790, 690 | | |

TABLE 2-1-continued $R_{14}-CONH-C_6H_4-CH=CH-\text{benzothiazol-2-yl}-X$ (3-substituted phenyl, trans vinyl to benzothiazole with positions 1(S), 2, 3(N), 4, 5, 6, 7)

| Compound No. | $R_{14}$ | X | m.p. (°C.) | Physical property values | Anti-SRS action [minimum effective conc. (M)] | Airway resistance increase inhibition (%) |
|---|---|---|---|---|---|---|
| 21 | cis-2-(COOH)cyclohexyl | " | 184~5 | IR 1715, 1660, 1525, 1200, 945, 790 | | |
| 22 | —(CH$_2$)$_2$COOH | " | 249~50 | IR 1710, 1650, 1580, 1180, 945, 800 | | |
| 23 | —(CH$_2$)$_3$COOH | " | 236~8 | IR 1710, 1655, 1425, 1200, 955, 780 | | |
| 24 | cis-CH=CH-COOH (maleic) | 5-Cl | 224~5 | IR 1695, 1550, 1400, 950, 855, 785 | | |
| 25 | 2-(COOH)phenyl | 5-Cl | 249~50 | IR 1700, 1580, 1230, 1065, 785 | | |
| 26 | cis-2-(COOH)cyclohexyl | " | 189~90 | IR 1700, 1520, 1350, 1200, 950, 800 | | |
| 27 | —(CH$_2$)$_2$COOH | " | 244~5 | IR 1690, 1650, 1580, 1200, 940, 800 | | |
| 28 | —(CH$_2$)$_3$COOH | " | 226~7 | IR 1705, 1660, 1540, 1200, 945, 800 | | |
| 29 | cis-CH=CH-COOH | 5-OMe | 199~200 | IR 1730, 1690, 1550, 1160, 850, 780 | | |
| 30 | 2-(COOH)phenyl | " | 198~9 | IR 1710, 1580, 1235, 950, 780 | | |
| 31 | cis-2-(COOH)cyclohexyl | " | >350 | IR 1700, 1550, 1405, 1160, 1120, 950, 790 | | |
| 32 | —(CH$_2$)$_2$COOH | " | 251~2 | IR 1700, 1650, 1180, 940, 680 | | |
| 33 | cis-2-(COOH)cyclohexyl | 6-OMe | 208~9 | IR 1710, 1660, 1600, 1540, 1495, 1260, 1180, 830 | | |
| 167 | HOOC-CH=CH- (trans) | H | 277~80 | NMR (CDCl$_3$—DMSO—d$_6$): $\delta$=6.56(2H,d), 6.83~6.9(11H, m), 10.07(1H, s) | $2 \times 10^{-7}$ | |
| 168 | HOOC— | " | 213~5 | NMR (CDCl$_3$—DMSO—d$_6$): $\delta$= 7.33~8.30(11H, m), 10.73(1H, broad s) | $10^{-7}$ | |
| 184 | EtOOC-CH=CH- (trans) | " | 180~1.5 | IR 1705, 1680, 1545, 1300, 760 | | |

TABLE 2-1-continued

R₁₄—CONH—C₆H₄—CH=CH—(benzothiazol-2-yl)—X

| Compound No. | R₁₄ | X | m.p. (°C.) | Physical property values | Anti-SRS action [minimum effective conc. (M)] | Airway resistance increase inhibition (%) |
|---|---|---|---|---|---|---|
| 185 | EtOOC— | " | 150~4 | IR 1730, 1700, 1300, 1208, 770 | | |
| 186 | EtOOCCH₂— | H | 134~7 | IR 1740, 1650, 1580, 1140, 1150, 940, 750 | | |
| 190 | (cis)-CH=CH-COOEt | " | 130~1 | IR 1685, 1615, 1580, 1210, 750 | | |
| 191 | 2-(COOCH₂CH₂CH(CH₃)₂)-phenyl | " | 132~3 | NMR (CDCl₃): δ=1.82(6H,d), 1.27~1.90(3H,m), 4.18(2H,m), 6.82~8.25(8H,m) | | |
| 192 | MeOOC(CH₂)₂— | " | 140~1 | IR 1735, 1680, 1580, 1550, 1420, 1155, 950, 760 | $5 \times 10^{-7}$ | |
| 193 | EtOOC(CH₂)₂— | " | 148~50 | IR 1720, 1680, 1540, 1175, 765 | | |
| 194 | (cyclopropyl)COOCH₂CH₂CH(CH₃)₂ | " | 149~51 | IR 1730, 1690, 1178, 953, 750 | | |
| 195 | (cis)-CH=CH-COOCH₂CH₂CH(CH₃)₂ | " | 82~3 | IR 1720, 1580, 1440, 1200, 755 | | |
| 214 | MeC(=CH)COONa | " | 171~3 | IR 1560, 1490, 1445, 1220, 950 | | |
| 215 | 2-(COONa)-phenyl | " | 274~7 | IR 1640, 1600, 1580, 1560, 1380, 743 | | |
| 216 | cis-2-(COONa)-cyclohexyl | " | 255~7 | IR 1640, 1550, 1483, 1405, 750 | | 85 |
| 217 | cis-2-(COONa)-cyclohexenyl | " | 150~60 | IR 1660, 1560, 1420, 1305, 750 | | |
| 218 | NaOOC(CH₂)₂— | " | 249~50 | IR 1665, 1580, 1415, 945, 755 | | |
| 219 | NaOOC(CH₂)₃— | " | 260~2 | IR 1650, 1550, 1410, 940, 750 | | |
| 220 | cis-4,5-diMe-2-(COONa)-cyclohexyl | " | 180~3 | IR 1705, 1560, 1405, 1310, 760 | | |
| 221 | 4,5-diMe-2-(COONa)-phenyl | H | 197~202 | IR 1625, 1560, 1400, 950, 760 | | |

TABLE 2-1-continued

Structure: R₁₄—CONH—(phenyl at 3-position)—CH=CH—(benzothiazole-2-yl with X substituent)

| Compound No. | R$_{14}$ | X | m.p. (°C.) | Physical property values | Anti-SRS action [minimum effective conc. (M)] | Airway resistance increase inhibition (%) |
|---|---|---|---|---|---|---|
| 222 | Me₂C(Et)—COONa | " | 150~5 | IR 1655, 1540, 945, 870, 750 | | |
| 223 | 1-ethylcyclohexyl-COONa | " | 168~71 | IR 1660, 1550, 1495, 1440, 1215, 955, 755 | | |
| 224 | Me₂C(Et)(Et)—COONa | " | 120~5 | IR 1650, 1540, 1210, 940, 750 | | 89 |
| 225 | C₆H₅—CH(iPr)—COONa | " | 125~30 | IR 1635, 1540, 1365, 925, 730 | | |
| 226 | Me(CH₂)₂CH(Et)—COONa | " | 125~30 | IR 1650, 1545, 1400, 950, 750 | | |
| 227 | Me(CH₂)₃CH(Et)—COONa | " | 180~3 | IR 1665, 1550, 950, 750 | 5 × 10⁻⁸ | |
| 228 | Me(CH₂)₄CH(Et)—COONa | " | 200~1 | IR 2910, 1655, 1545, 1305, 750 | | |
| 229 | Me₂CH—C(Me)(Et)—COONa | " | 145~50 | IR 1650, 1540, 1210, 950, 750 | | |
| 230 | CH=CH—COONa | 5-Me | 225~9 | IR 1680, 1590, 1440, 1305, 950, 790 | | |
| 231 | 2-carboxyphenyl (COONa) | " | 273~5 | IR 1660, 1580, 1550, 945 | 5 × 10⁻⁹ | |
| 232 | cis-2-methylcyclohexyl-COONa | " | 290~303 | IR 1680, 1590, 1530, 1400, 1300, 950, 785 | | 83 |

TABLE 2-1-continued

Structure: $R_{14}-CONH$-phenyl-CH=CH-benzothiazole (2-position), with X substituent on benzothiazole ring (positions 4,5,6,7)

| Compound No. | $R_{14}$ | X | m.p. (°C.) | Physical property values | Anti-SRS action [minimum effective conc. (M)] | Airway resistance increase inhibition (%) |
|---|---|---|---|---|---|---|
| 233 | $NaOOC(CH_2)_2-$ | " | 228~31 | IR 1660, 1565, 1410, 950, 790 | | |
| 234 | $NaOOC(CH_2)_3-$ | 5-Me | 213~5 | IR 1655, 1570, 1535, 1410, 1200 | | |
| 235 | cis-cyclohexyl-COONa | 5-COOMe | 330~5 | IR 1700, 1585, 1540, 1400, 1300, 760 | | |
| 236 | cis-CH=CH-COONa | 5-Cl | 257~60 | IR 1630, 1580, 1490, 1430, 955 | | |
| 237 | phenyl-COONa (ortho) | " | 293~6 | IR 1680, 1590, 1565, 1490, 1390 | | |
| 238 | cis-cyclohexyl-COONa | " | 284~94 | IR 1680, 1580, 1530, 1400, 950, 790 | | |
| 239 | $NaOOC(CH_2)_2-$ | " | 230~4 | IR 1655, 1580, 1540, 1430, 940 | | |
| 240 | $NaOOC(CH_2)_3-$ | " | 215~7 | IR 1650, 1570, 1540, 1430, 940 | | |
| 241 | cis-CH=CH-COONa | 5-OMe | 215~7 | IR 1630, 1585, 1430, 1280, 950, 800 | | |
| 242 | phenyl-COONa (ortho) | " | 295~8 | IR 1675, 1590, 1540, 1490, 1390 | | |
| 243 | cis-cyclohexyl-COONa | " | >350 | IR 1560, 1400, 1270, 1190, 800 | | |
| 244 | $NaOOC(CH_2)_2-$ | " | 241~3 | IR 1655, 1550, 1420, 950, 725 | | |
| 245 | cis-cyclohexyl-COONa | 6-OMe | 260~5 | IR 1680, 1585, 1400, 1260, 950, 800 | | |
| 415 | cis-CH=CH-COOH · Tris | H | 179~80 | IR 1625, 1560, 1350, 1330, 1060, 750 | | |
| 416 | trans-HOOC-CH=CH- · Tris | " | 108~9 | IR 1625, 1615, 1550, 1380, 1050, 750 | | |

TABLE 2-1-continued

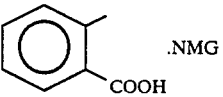

| Compound No. | $R_{14}$ | X | m.p. (°C.) | Physical property values | Anti-SRS action [minimum effective conc. (M)] | Airway resistance increase inhibition (%) |
|---|---|---|---|---|---|---|
| 417 | 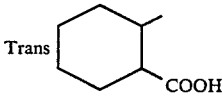 | " | 135~40 224~5 | IR 1650, 1550, 1475, 1080, 755 | | |
| 418 | 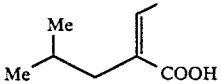 | " | 95~6 (decomposition) | IR 1660, 1550, 1400, 1080, 750 | | |
| 419 | HOOC(CH$_2$)$_2$—.Tris | " | 162~3 | IR 1630, 1605, 1600, 1580, 1410, 1060, 750 | | |
| 445 | 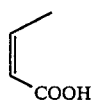 | " | 133~5 | IR 1695, 1630, 1520, 1190, 750 | | |

TABLE 2-2

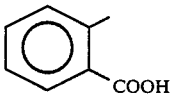

| Compound No. | $R_{14}$ | X | m.p. (°C.) | Physical property values (IR) | Anti-SRS action [minimum effective conc. (M)] | Airway resistance increase inhibition (%) |
|---|---|---|---|---|---|---|
| 34 | 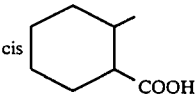 | H | 199~200 | 1740, 1720, 1700, 1620, 1540, 1400, 845, 725 | $2 \times 10^{-8}$ | |
| 35 | 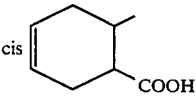 | " | 201~5 | 1720, 1620, 1575, 1550, 1242, 735 | | |
| 36 | cis  | " | 205~6 | 1695, 1680, 1540, 1440, 1280, 945, 750 | | |
| 37 | cis  | " | 204~5 | 1690, 1540, 1410, 1200, 940, 755 | | |
| 38 | —(CH$_2$)$_2$COOH | " | 237~8 | 1690, 1650, 1530, 1405, 735 | | |
| 39 | —(CH$_2$)$_3$COOH | " | 190~2 | 1700, 1650, 1595, 1400, 950, 725 | | |

TABLE 2-2-continued

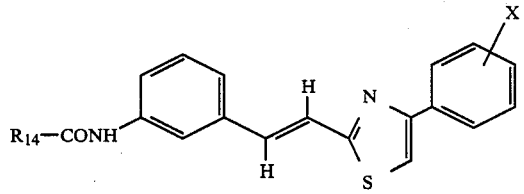

| Compound No. | R14 | X | m.p. (°C.) | Physical property values (IR) | Anti-SRS action [minimum effective conc. (M)] | Airway resistance increase inhibition (%) |
|---|---|---|---|---|---|---|
| 40 | cis (norbornane-COOH) | " | 159~60 | 3300, 2950, 1700, 1545, 1190, 950, 725 | | |
| 41 | Me, Me cis cyclohexane-COOH | " | 202~3 | 1700, 1542, 1195, 945, 755 | | |
| 42 | Me, Me benzene-COOH | " | 184~5 | 1685, 1660, 1600, 1328, 950, 730 | | |
| 43 | 1-ethylcyclohexane-COOH | " | 182~4 | 1660, 1550, 1490, 1440, 1210, 955, 755 | | |
| 44 | CH=CH-COOH | p-Cl | 204~7 | 1695, 1615, 1530, 1395, 1080, 945, 840, 735 | | |
| 45 | benzene-COOH | " | 218~20 | 1720, 1640, 1620, 1610, 1500, 1245, 780, 760 | | |
| 46 | cis cyclohexane-COOH | " | 214~5 | 1680, 1580, 1470, 1400, 940, 825, 770 | | |
| 47 | cis cyclohexene-COOH | " | 210~3 | 1685, 1580, 1540, 1200, 940, 770 | | |
| 48 | —(CH2)3COOH | " | 179~81 | 1685, 1655, 1595, 1530, 1400, 950, 740 | | |
| 49 | cis cyclohexane-COOH | p-Me | 203~4 | 1692, 1540, 1180, 950, 775 | | |
| 50 | cis cyclohexene-COOH | " | 202~3 | 1690, 1540, 1200, 945, 775 | | |

TABLE 2-2-continued

[Structure: R14—CONH—(phenyl, meta-substituted)—CH=CH—(thiazole: N, S, with =CH)—C(=CH-)—phenyl-X]

| Compound No. | R14 | X | m.p. (°C.) | Physical property values (IR) | Anti-SRS action [minimum effective conc. (M)] | Airway resistance increase inhibition (%) |
|---|---|---|---|---|---|---|
| 51 | cis-2-methylcyclohexane-1-COOH | m-Me | 197~8 | 1690, 1540, 1180, 940, 770 | | |
| 52 | cis-2-methylcyclohexane-1-COOH | p-CMe | 187~8 | 1685, 1530, 1250, 1175, 770 | | |
| 53 | cis-2-methylcyclohexane-1-COOH | p-COOEt | 204~5 | 1705, 1545, 1415, 1280 | | |
| 246 | cis-CH=CH-CH(CH3)-COONa (butenoate) | H | 225~8 | 1650, 1560, 1440, 950, 735 | | |
| 247 | 2-COONa-phenyl | " | 266~70 | 1660, 1580, 1550, 1400, 1380, 950, 730 | | |
| 248 | cis-2-methylcyclohexane-1-COONa | " | 234~5 | 1642, 1540, 1400, 955, 735 | | 85 |
| 249 | cis-2-methylcyclohex-3-ene-1-COONa | H | 149~50 | 1650, 1540, 1400, 955, 720 | | |
| 250 | NaOOC(CH2)2— | " | 295~8 | 1645, 1555, 1430, 1410, 815, 735 | | |
| 251 | NaOOC(CH2)3— | " | 275~7 | 1660, 1600, 1540, 1400, 955, 730 | | |
| 252 | cis-3,4-dimethyl-6-methylcyclohexane-1-COONa | " | 170~4 (decomposition) | 1665, 1550, 1405, 950, 730 | | |
| 253 | 3,4-dimethyl-6-methylphenyl-1-COONa | " | 150~2 (decomposition) | 1650, 1580, 1480, 1400, 950 | $5 \times 10^{-8}$ | |
| 254 | 1-ethylcyclohexane-1-COONa | " | 136~9 | 1660, 1550, 1490, 1440, 1210, 955, 755 | | |

TABLE 2-2-continued

| Compound No. | R₁₄ | X | m.p. (°C.) | Physical property values (IR) | Anti-SRS action [minimum effective conc. (M)] | Airway resistance increase inhibition (%) |
|---|---|---|---|---|---|---|
| 255 | (cis-CH=CH-CH₂-COONa) | p-Cl | 225~8 | 1560, 1470, 1085, 945, 735 | | |
| 256 | o-(COONa)phenyl | " | 307~20 | 1680, 1610, 1590, 1530, 1385, 705 | | |
| 257 | cis-cyclohexane-1,2-COONa | " | 273~5 | 1660, 1550, 1465, 1080, 945, 825, 740 | | |
| 258 | cis-cyclohexene-COONa | " | 159~62 | 1660, 1560, 1470, 1400, 1085, 740 | | |
| 259 | NaOOC(CH₂)₃— | " | 288~91 | 1660, 1600, 1550, 1400, 1095, 955, 745 | | |
| 260 | cis-cyclohexane-1,2-COONa | p-Me | 255~6 | 1665, 1560, 1480, 1405, 950, 740 | | |
| 261 | cis-cyclohexene-COONa | " | 152~3 | 1660, 1550, 1480, 1405, 950, 740 | | |
| 262 | cis-cyclohexane-1,2-COONa | m-Me | 170~80 | 1660, 1540, 1400, 950, 780, 730 | | |
| 263 | " | p-CMe | <280 | 1685, 1590, 1480, 1240, 745 | | |
| 264 | " | p-COOMe | <340 | 1690, 1590, 1540, 1400, 1290, 740 | | |

TABLE 2-3

$$R^{14}-CONH-\text{[phenyl]}-CH=CH-\text{[thiazole]}-R_1$$

| Compound No. | R14 | R1 | m.p. (°C.) | Physical property values (IR) | Anti-SRS action [minimum effective conc. (M)] | Airway resistance increase inhibition (%) |
|---|---|---|---|---|---|---|
| 54 | cis-CH=CH-COOH | Me | 157~8 | 1700, 1620, 1550, 965, 855 | 5 × 10⁻⁷ | |
| 55 | —(CH₂)₂COOH | " | 199~200 | 1720, 1640, 1530, 1080, 945 | | |
| 56 | —(CH₂)₃COOH | " | 208~10 | 1705, 1645, 1525, 1080, 950 | | |
| 57 | cis-CH=CH-COOH | Et | 149~50 | 1690, 1620, 1530, 850 | | |
| 58 | o-C₆H₄-COOH | " | 181~3 | 1720, 1580, 1550, 1245, 780 | | |
| 59 | cis-cyclohexyl-COOH | " | 192~3 | 1690, 1655, 1540, 1200, 790 | | |
| 60 | —(CH₂)₂COOH | " | 191~2 | 1690, 1540, 1320, 1190, 780 | | |
| 61 | —(CH₂)₃COOH | " | 146~7 | 1705, 1643, 1530, 1180, 950, 780 | | |
| 62 | cis-CH=CH-COOH | CH₃(CH₂)₂— | 151~2 | 1700, 1620, 1550, 1410, 860 | | |
| 63 | o-C₆H₄-COOH | " | 180~1 | 1720, 1625, 1580, 1245, 781 | | |
| 64 | cis-cyclohexyl-COOH | CH₃(CH₂)₂— | 171~2 | 1685, 1540, 1200, 785 | | |
| 65 | —(CH₂)₂COOH | " | 173~4 | 1685, 1540, 1320, 1190, 950, 775 | | |
| 66 | —(CH₂)₃COOH | " | 130~1 | 1715, 1640, 1440, 1185, 950, 775 | | |
| 67 | cis-CH=CH-COOH | CH₃(CH₂)₃— | 151~3 | 1695, 1615, 1545, 1400, 950, 855 | | |
| 68 | o-C₆H₄-COOH | " | 168~9 | 1715, 1650, 1575, 1480, 1240, 950, 780 | | |
| 69 | —(CH₂)₂COOH | " | 149~51 | 1700, 1680, 1540, 1480, 1320, 950, 755 | | |
| 70 | —(CH₂)₃COOH | " | 81~3 | 1680, 1650, 1600, 1555, 1485, 1135, 950 775 | | |
| 71 | cis-CH=CH-COOH | CH₃(CH₂)₄— | 143~4 | 1700, 1550, 1410, 970, 860 | | |
| 72 | o-C₆H₄-COOH | " | 178~9 | 1720, 1620, 1575, 1550, 1415, 1240, 960 775 | | |
| 73 | cis-cyclohexyl-COOH | " | 161~3 | 1690, 1540, 1440, 1410, 1200, 945 | | |

TABLE 2-3-continued $$R^{14}-CONH-\text{[phenyl]}-CH=CH-\text{[thiazole]}-R_1$$

| Compound No. | R₁₄ | R₁ | m.p. (°C.) | Physical property values (IR) | Anti-SRS action [minimum effective conc. (M)] | Airway resistance increase inhibition (%) |
|---|---|---|---|---|---|---|
| 74 | cis-2-methylcyclohexyl-COOH | " | 153~5 | 1690, 1540, 1200, 945 | | |
| 75 | —(CH₂)₂COOH | " | 149~51 | 1710, 1650, 1580, 1440, 1180, 945 | | |
| 76 | —(CH₂)₃COOH | " | 87~8 | 1680, 1658, 1605, 1340, 1200, 780 | | |
| 77 | (vinyl)-COOH | CH₃(CH₂)₅— | 142~3 | 1700, 1620, 1555, 1535, 1405, 865 | | |
| 78 | 2-COOH-phenyl | " | 175~6 | 1710, 1625, 1580, 1550, 1250 | | |
| 79 | —(CH₂)₂COOH | " | 145~6 | 1720, 1660, 1585, 1530, 1440 | | |
| 80 | —(CH₂)₃COOH | " | 140~1 | 1715, 1645, 1580, 1530 | | |
| 81 | (vinyl)-COOH | CH₃(CH₂)₈— | 140~1 | 1700, 1555, 1407, 860 | | |
| 82 | 2-COOH-phenyl | " | 155~7 | 1720, 1623, 1580, 1243, 965, 780 | | |
| 83 | —(CH₂)₂COOH | " | 144~5 | 1720, 1660, 1530, 1180, 960, 780 | | |
| 84 | —(CH₂)₃COOH | " | 127~8 | 1710, 1653, 1530, 785 | | |
| 85 | cis-2-methylcyclohexyl-COOH | CH₃(CH₂)₇— | 160~2 | 1685, 1540, 1200, 940 | | |
| 86 | (vinyl)-COOH | (CH₃)₃C— | 185~6 | 1700, 1550, 1405, 960, 860 | | |
| 87 | 2-COOH-phenyl | " | 167~8 | 1720, 1580, 1230, 955, 780 | | |
| 88 | —(CH₂)₂COOCH | " | 171~2 | 1720, 1660, 1165, 960, 790 | | |
| 89 | —(CH₂)₃COOCH | " | 139~40 | 1705, 1680, 1550, 1220, 960, 790 | | |
| 90 | (vinyl)-COOH | (CH₃)₂CH— | 148~9 | 1695, 1615, 1540, 1300, 845 | | |
| 91 | Me₂CH-CH=C(COOH)- | " | 118~20 | 1690, 1620, 1525, 950 | | |
| 92 | 2-COOH-phenyl | " | 182~3 | 1720, 1580, 1240, 853, 778 | | |
| 93 | cis-2-methylcyclohexyl-COOH | " | 169~70 | 1705, 1640, 1533, 1185, 955 | | |
| 94 | —(CH₂)₂COOH | " | 158~9 | 1700, 1680, 1580, 1410, 955, 790, 740 | | |
| 95 | —(CH₂)₃COOH | " | 143~4 | 3270, 1710, 1640, 1440, 1180, 940 | | |

TABLE 2-3-continued $R^{14}-CONH-C_6H_4-CH=CH-C(=N)-S-CH=C-R_1$ (thiazole ring)

| Compound No. | R14 | R1 | m.p. (°C.) | Physical property values (IR) | Anti-SRS action [minimum effective conc. (M)] | Airway resistance increase inhibition (%) |
|---|---|---|---|---|---|---|
| 96 | 1-ethylcyclohexane-1-COOH | " | 175~6 | 1690, 1550, 1450, 960, 785 | | |
| 97 | Me₂C(CH₂-)COOH (2,2-dimethylpropanoic acid branch) | " | 175~6 | 2950, 1710, 1650, 1180, 950, 755 | | |
| 98 | Me(CH₂)₃CH(Et)COOH | " | 160~1 | 1707, 1640, 1543, 1170, 960, 783 | | |
| 99 | PhCH(Et)COOH | " | 199~200 | 1705, 1660, 1540, 960, 695 | | |
| 100 | MeCH₂CH(Et)COOH | " | 155~6 | 1705, 1655, 1540, 1170, 955, 780 | | |
| 101 | Me(CH₂)₃CH(Et)COOH | " | 147~8 | 1705, 1657, 1165, 955, 780 | | |
| 102 | Me₂C(Et)COOH | " | 154~5 | 1680, 1540, 1405, 1190, 950, 785 | | |
| 103 | Me₂CHCH(Me)C(Et)(COOH)- | " | 175~6 | 1680, 1540, 950, 790 | | |
| 104 | Me₂C(Et)COOH | (CH₃)₂CH— | 155~6 | 3300, 2950, 1680, 1540, 950, 780 | | |
| 265 | cis-CH=CH-COONa | Me | 156~7 | 1630, 1550, 1440, 940, 850, 765 | | |
| 266 | " | Et | 135~40 | 1660, 1555, 1440, 950, 850, 780 | | |
| 267 | o-Me-C₆H₄-COONa | " | 152~5 | 1650, 1560, 1385, 955, 780 | | |
| 268 | cis-2-Me-cyclohexane-COONa | " | 144~6 | 1680, 1547, 1405, 950, 780 | | |
| 269 | NaOOC(CH₂)₂— | " | 165~70 | 1660, 1555, 1410, 950, 785 | | |
| 270 | NaOOC(CH₂)₃— | " | 210~1 | 1645, 1550, 1410, 950, 785 | | |
| 271 | cis-CH=CH-COONa | —(CH₂)₂CH₃ | 118~20 | 1660, 1560, 1440, 950, 780 | | |

TABLE 2-3-continued $$R^{14}-CONH-\text{(phenyl)}-CH=CH-\text{(thiazole)}-R_1$$

| Compound No. | $R_{14}$ | $R_1$ | m.p. (°C.) | Physical property values (IR) | Anti-SRS action [minimum effective conc. (M)] | Airway resistance increase inhibition (%) |
|---|---|---|---|---|---|---|
| 272 | 2-(COONa)phenyl | " | 161~3 | 1640, 1585, 1580, 950, 780 | | |
| 273 | cis-2-(COONa)cyclohexyl | " | 137~40 | 1660, 1550, 1405, 950, 780 | | |
| 274 | $NaOOC(CH_2)_2-$ | " | 183~5 | 1660, 1550, 1410, 1190, 950, 780 | $10^{31\ 7}$ | |
| 275 | $NaOOC(CH_2)_3-$ | " | 195~7 | 1650, 1555, 1410, 950, 785 | | |
| 276 | (COONa)vinyl | $-(CH_2)_3CH_3$ | 123~7 | 1695, 1615, 1545, 1400, 950, 855 | | |
| 277 | 2-(COONa)phenyl | $-(CH_2)_3CH_3$ | 120~5 | 1650, 1600, 1580, 1560, 1385, 1325, 955 | | |
| 278 | $NaOOC(CH_2)_2-$ | " | 185~90 | 1665, 1560, 1410, 950, 785 | | |
| 279 | $NaOOC(CH_2)_3-$ | " | 187~92 | 1650, 1580, 1555, 1435, 1410, 955 | | |
| 280 | (COONa)vinyl | $-(CH_2)_4CH_3$ | 135~8 | 1660, 1555, 1430, 948, 850 | | |
| 281 | 2-(COONa)phenyl | " | 118~20 (decomposition) | 1660, 1545, 1410, 955, 780 | | |
| 282 | cis-2-(COONa)cyclohexyl | " | 135~40 | 1660, 1545, 1410, 950, 780 | | |
| 283 | cis-2-(COONa)cyclohexenyl | $-(CH_2)_4CH_3$ | 95~99 | 1660, 1560, 1410, 950, 780 | | |
| 284 | $NaOOC(CH_2)_2-$ | " | 170~6 | 1660, 1555, 1410, 945, 780 | | |
| 285 | $NaOOC(CH_2)_3-$ | " | 225~6 | 1648, 1545, 1410, 948, 787 | | |
| 286 | (COONa)vinyl | $-CH_2)_5CH_3$ | 115~7 | 1665, 1570, 1440, 955, 860 | | |
| 287 | 2-(COONa)phenyl | " | 118~20 | 1650, 1600, 1580, 1560, 1390, 955 | $2 \times 10^{-5}$ | |
| 288 | $NaOOC(CH_2)_2-$ | " | 178~80 | 1660, 1555, 1410, 950 | | |
| 289 | $NaOOC(CH_2)_3-$ | " | 167~70 | 1650, 1550, 1410, 955 | | |
| 290 | (COONa)vinyl | $-(CH_2)_6CH_3$ | 125~7 | 1660, 1560, 1440, 950, 850, 780 | | |
| 291 | 2-(COONa)phenyl | " | 114~6 | 1650, 1580, 1390, 955, 780 | $10^{-7}$ | |
| 292 | $NaOOC(CH_2)_2-$ | " | 150~5 | 1660, 1558, 1410, 950, 785 | | |

TABLE 2-3-continued $$R^{14}-CONH-C_6H_4-CH=CH-\underset{S}{\overset{N}{\diagdown}}\!\!=\!\!R_1$$

| Compound No. | $R_{14}$ | $R_1$ | m.p. (°C.) | Physical property values (IR) | Anti-SRS action [minimum effective conc. (M)] | Airway resistance increase inhibition (%) |
|---|---|---|---|---|---|---|
| 293 | NaOCC(CH$_2$)$_3$— | " | 199~200 | 1650, 1555, 1415, 955, 790 | | |
| 294 | cis-2-methylcyclohexyl-COONa | —(CH$_2$)$_7$CH$_3$ | 171~3 | 1650, 1540, 1400, 950, 780 | | |
| 295 | cyclohexenyl-COONa | —C(CH$_3$)$_3$ | 154~6 | 1660, 1560, 1440, 1350, 950, 780 | | |
| 296 | o-methylphenyl-COONa | " | 168~71 | 1640, 1580, 1560, 1385, 955, 740 | | |
| 297 | NaOOC(CH$_2$)$_2$— | " | 174~7 | 1660, 1600, 1560, 1415, 955 | | |
| 298 | NaOOC(CH$_2$)$_3$— | " | 192~3 | 1660, 1605, 1560, 1415, 955 | 5 × 10$^{-5}$ | |
| 299 | cyclohexenyl-COONa | —CH(CH$_3$)$_2$ | 140~5 | 1660, 1560, 1440, 1350, 950, 780 | | |
| 300 | o-methylphenyl-COONa | " | 145~50 | 1650, 1600, 1555, 1380, 950, 740 | | |
| 301 | cis-2-methylcyclohexyl-COONa | " | 130~2 | 1660, 1540, 1400, 955, 780 | | |
| 302 | NaOOC(CH$_2$)$_2$— | " | 207~10 | 1660, 1550, 1410, 945, 780 | | |
| 303 | NaOOC(CH$_2$)$_3$— | —CH(CH$_3$)$_2$ | 260~70 | 1650, 1555, 1408, 943, 690 | | |
| 304 | 1-ethylcyclohexyl-COONa | " | 150~3 | 1660, 1550, 1445, 1400, 1210, 955, 780 | | |
| 305 | Me$_2$C-COONa | " | 120~6 | 1660, 1550, 1410, 950, 780 | | |
| 306 | Me-CH$_2$-CH(COONa)- | " | 100~5 | 1650, 1540, 1400, 950, 780 | | |
| 307 | PhCH(COONa)- | " | 127~30 | 1660, 1575, 1380, 930, 710 | 2 × 10$^{-9}$ | |
| 308 | Me(CH$_2$)$_3$CH(COONa)- | " | 120~5 | 1660, 1550, 1260, 960, 785 | | 96 |
| 309 | Me(CH$_2$)$_4$CH(COONa)- | " | 55~60 | 1650, 1550, 1400, 950, 780 | | |
| 310 | EtMeC(COONa)- | " | 130~5 | 1650, 1540, 1400, 950, 775 | | 93 |

TABLE 2-3-continued $$R^{14}-CONH-\text{[phenyl]}-CH=CH-\text{[thiazole with }R_1\text{]}$$

| Compound No. | R14 | R1 | m.p. (°C.) | Physical property values (IR) | Anti-SRS action [minimum effective conc. (M)] | Airway resistance increase inhibition (%) |
|---|---|---|---|---|---|---|
| 311 | Me-CH(Me)-C(Me)(Et)-COONa | " | 120~3 | 1650, 1540, 1400, 950, 780 | | |
| 312 | Et-C(Me)(Et)-COONa | " | 90~95 | 1650, 1540, 1400, 950, 780 | | |
| 446 | Et-C(Et)(Et)-COOH | —(CH2)2CH3 | 159~60 | 1670, 1520, 1190, 960, 760 | | |
| 447 | Et-C(Me)(Et)-COOH | " | 155~6 | 1670, 1540, 1410, 950, 780 | | |
| 448 | Me-CH(Me)-C(Me)(Et)-COOH | " | 164~5 | 1680, 1580, 1410, 1200, 955 | | |

TABLE 2-4

$$R_{14}-CONH-\text{[phenyl]}-CH=CH-\text{[thiazole with }R_1, R_2\text{]}$$

| Compound No. | R14 | R1, R2 | m.p. (°C.) | Physical property values (IR) | Anti-SRS action [minimum effective conc. (M)] | Airway resistance increase inhibition (%) |
|---|---|---|---|---|---|---|
| 105 | cis-CH=CH-COOH | Me, Me | 150~2 | 1705, 1620, 1580, 1540, 940, 840 | | |
| 106 | o-C6H4-COOH | " | 181~3 | 1700, 1650, 1545, 1255, 785 | | |
| 107 | cis cyclohexane-COOH | " | 175~7 | 1660, 1600, 1545, 1210, 960, 780 | | |
| 108 | trans cyclohexane-COOH | " | 195~200 | 1705, 1655, 1605, 1545, 1180, 960, 780 | | |
| 109 | cis cyclohexene-COOH | " | 197~200 | 1680, 1580, 1540, 1430, 1215, 950, 780 | | |
| 110 | —(CH2)2COOH | " | 203~4 | 1710, 1660, 1600, 1550, 1230, 790 | | |
| 111 | —(CH2)3COOH | " | 166~9 | 1700, 1660, 1600, 1550, 1210, 945 | | |

TABLE 2-4-continued

Structure: $R_{14}-CONH$ — (3-substituted phenyl) — CH=CH — (thiazole with $R_1$, $R_2$)

| Compound No. | $R_{14}$ | $R_1, R_2$ | m.p. (°C.) | Physical property values (IR) | Anti-SRS action [minimum effective conc. (M)] | Airway resistance increase inhibition (%) |
|---|---|---|---|---|---|---|
| 112 | cis-bicyclo-COOH | " | 206~7 | 1675, 1540, 1405, 1200, 940, 785 | | |
| 113 | (1-ethyl-cyclohexyl)-COOH | " | 167~70 | 1650, 1540, 1440, 780 | | |
| 114 | Me,Me-C(COOH)- | " | 199~200 | 1680, 1540, 1200, 950, 780 | | |
| 115 | CH=CH-COOH (cis) | Et, Me | 173~4 | 1670, 1540, 1410, 1260, 955, 800 | | |
| 116 | 2-COOH-phenyl | " | 186~7 | 1720, 1580, 1250, 950, 780 | | |
| 117 | cis-(2-methylcyclohexyl)-COOH | " | 186~7 | 3320, 2910, 1690, 1540, 1410, 945, 780 | | |
| 118 | —(CH$_2$)$_2$COOH | " | 215~6 | 1680, 1540, 1300, 950, 780 | | |
| 119 | —(CH$_2$)$_3$COOH | " | 163~4 | 3270, 1710, 1650, 1530, 1200, 780 | | |
| 120 | cis-Me,Me-cyclohexyl-COOH | " | 178~9 | 1700, 1660, 1540, 1210, 780 | | |
| 121 | Me,Me-phenyl-COOH | " | 200~1 | 1703, 1650, 1540, 1250, 780 | | |
| 122 | (1-ethylcyclohexyl)-COOH | " | 211~2 | 1680, 1540, 1410, 950, 785 | | |
| 123 | Me,Me-C(COOH)- | " | 209~10 | 1677, 1540, 1200, 950, 785 | | |
| 124 | Me-CH$_2$-CH$_2$-CH(COOH)- | " | 184~5 | 1700, 1655, 1600, 1540, 1175, 960, 785 | | |
| 125 | CH=CH-COOH (cis) | CH$_3$(CH$_2$)$_2$—, Et | 144~5 | 1720, 1600, 1550, 948, 845 | | |
| 126 | 2-COOH-phenyl | " | 142~3 | 1700, 1438, 1380, 1100, 710 | | |
| 127 | cis-(2-methylcyclohexyl)-COOH | " | 181~3 | 1690, 1650, 1540, 1210, 950, 780 | | |

TABLE 2-4-continued

Structure: R14—CONH—(phenyl)—CH=CH—(thiazole with R1, R2)

| Compound No. | R14 | R1, R2 | m.p. (°C.) | Physical property values (IR) | Anti-SRS action [minimum effective conc. (M)] | Airway resistance increase inhibition (%) |
|---|---|---|---|---|---|---|
| 128 | —(CH$_2$)$_2$COOH | CH$_3$(CH$_2$)$_2$—, Et | 160~1 | 1710, 1660, 1605, 1545, 960, 785 | | |
| 129 | —(CH$_2$)$_3$COOH | " | 81~2 | 1685, 1660, 1605, 1340, 1195, 780 | | |
| 130 | 2-COOH-phenyl | C$_6$H$_5$—, —(CH$_2$)$_3$CH$_3$ | 204~8 | 1720, 1620, 1580, 1545, 1235, 950, 780 | | |
| 131 | cis 2-COOH-cyclohexyl | " | 133~5 | 1680, 1580, 1530, 1410, 1200, 950, 785 | | |
| 132 | 2-COOH-phenyl | Me, —(CH$_2$)$_3$CH$_3$ | 173~6 | 1720, 1620, 1580, 1545, 1240, 955, 780 | | |
| 133 | cis 2-COOH-cyclohexyl | " | 164~7 | 1700, 1655, 1600, 1540, 1080, 960, 780 | | |
| 134 | cis 2-COOH-cyclohexyl | —(CH$_2$)$_2$CH$_3$, Et | 161~3 | 1690, 1650, 1540, 1210, 950, 780 | | |
| 135 | cis 2-COOH-cyclohexyl | —COOEt, H | 202~4 | 1690, 1545, 1415, 1205, 950, 790 | | |
| 136 | cis-CH=CH-COOH | —(CH$_2$)$_4$— | 190~3 | 1698, 1541, 1405, 850, 735 | | |
| 137 | —(CH$_2$)$_2$COOH | " | 236~7 | 1680, 1595, 1530, 1250, 804 | | |
| 169 | HOOC—CH=CH— | Me, Me | 255~60 | 1710, 1670, 1600, 1545, 1250, 970, 785 | | |
| 187 | EtOOC—CH=CH— | " | 163~4 | 1700, 1680, 1550, 1295, 1155, 780 | | |
| 313 | cis-CH=CH-COONa | " | 163~7 | 1620, 1550, 1480, 1350, 1210, 940, 850 | | |
| 314 | 2-COONa-phenyl | Me, Me | 165~7 | 1655, 1580, 1550, 1385, 950, 780 | | |
| 315 | cis 2-COONa-cyclohexyl | " | 177~9 | 1675, 1550, 1440, 1410, 950, 780 | | |
| 316 | Trans 2-COONa-cyclohexyl | " | 242~6 | 1660, 1550, 1405, 945, 775 | | |
| 317 | cis 2-COONa-cyclohexenyl | " | 177~80 | 1660, 1575, 1540, 1430, 780 | | 85 |

TABLE 2-4-continued $R_{14}$—CONH—[3-phenyl]—CH=CH—[thiazole with $R_1$, $R_2$]

| Compound No. | $R_{14}$ | $R_1$, $R_2$ | m.p. (°C.) | Physical property values (IR) | Anti-SRS action [minimum effective conc. (M)] | Airway resistance increase inhibition (%) |
|---|---|---|---|---|---|---|
| 318 | NaOOC(CH$_2$)$_2$— | " | 203~6 | 1650, 1630, 1580, 1410, 950, 780 | | |
| 319 | NaOOC(CH$_2$)$_3$— | " | 201~3 | 1655, 1555, 1410, 950, 780 | | |
| 320 | cyclohexyl-Et-COONa | " | 167~70 | 1650, 1540, 1440, 1250, 950, 775 | | |
| 321 | Me,Me-C(Et)-COONa | " | 155~60 | 1660, 1540, 1400, 950, 780 | | |
| 322 | cyclohexenyl-COONa | Et, Me | 141~2 | 1660, 1555, 1435, 1350, 945, 780 | | |
| 323 | 2-methylphenyl-COONa | " | 151~3 | 1650, 1560, 1385, 950, 780 | | |
| 324 | cis-2-methylcyclohexyl-COONa | " | 150~5 | 1665, 1545, 1405, 955, 780 | | |
| 325 | NaOOC(CH$_2$)$_2$— | " | 194~6 | 1660, 1560, 1410, 945 | | |
| 326 | NaOOC(CH$_2$)$_3$— | " | 205~10 | 1645, 1550, 1410, 950, 830, 780 | | |
| 327 | cis-Me,Me-dimethylcyclohexyl-COONa | Et, Me | 163~8 (decomposition) | 1665, 1550, 1410, 955, 785 | | |
| 328 | Me,Me-dimethylphenyl-COONa | " | 180~5 | 1650, 1550, 1405, 1320, 950, 780 | 5 × 10$^{-9}$ | |
| 329 | cyclohexyl-Et-COONa | " | 145~50 | 1655, 1545, 1440, 1210, 950, 780 | | |
| 330 | Me,Me-C(Me)-COONa | " | 145~50 | 1660, 1545, 1410, 1360, 950, 780 | | |
| 331 | Me-CH(Et)-COONa | " | 130~5 | 1650, 1540, 1400, 950, 780 | | |
| 332 | cyclohexenyl-COONa | CH$_3$(CH$_2$)$_2$—, Et | 153~7 | 1660, 1560, 1440, 950, 850, 780 | 10$^{-7}$ | |
| 333 | 2-methylphenyl-COONa | " | 195~7 | 1640, 1550, 1383, 950, 780 | | |
| 334 | cis-2-methylcyclohexyl-COONa | " | 163~6 | 1655, 1540, 1405, 950, 780 | | |

TABLE 2-4-continued

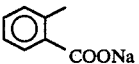

| Compound No. | R14 | R1, R2 | m.p. (°C.) | Physical property values (IR) | Anti-SRS action [minimum effective conc. (M)] | Airway resistance increase inhibition (%) |
|---|---|---|---|---|---|---|
| 335 | NaOOC(CH$_2$)$_2$— | " | 164~6 | 1660, 1550, 1405, 950, 775 | | |
| 336 | NaOOC(CH$_2$)$_3$— | " | 188~9 | 1650, 1550, 1405, 950, 780 | | |
| 337 | 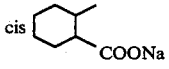 (2-COONa phenyl) | C$_6$H$_5$—, —(CH$_2$)$_3$CH$_3$ | 188~92 | 1580, 1550, 1480, 1385, 770, 690 | | |
| 338 | cis 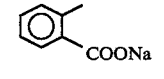 (2-COONa cyclohexyl) | " | 153~5 | 1660, 1545, 1480, 1405, 770, 690 | | |
| 339 | (2-COONa phenyl) | Me, —(CH$_2$)$_3$CH$_3$ | 138~41 | 1645, 1545, 1380, 950, 780 | | |
| 340 | cis (2-COONa cyclohexyl) | Me, —(CH$_2$)$_3$CH$_3$ | 165~9 | 1660, 1540, 1440, 1405, 960, 780 | | |
| 341 | " | —(CH$_2$)$_2$CH$_3$, Et | 163~6 | 1655, 1540, 1405, 1300, 950, 780 | | |
| 342 | " | —COOEt, H | 177~80 | 1710, 1670, 1545, 1400, 1220, 780 | | |
| 343 | 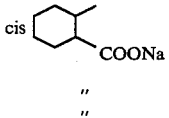 (cis-CH=CH-COONa) | —(CH$_2$)$_4$— | 240~50 | 1660, 1550, 1430, 1310, 810 | | |
| 344 | NaOOC(CH$_2$)$_2$— | " | 250~60 | 1665, 1585, 1520, 1400, 950, 810 | | |

TABLE 2-5

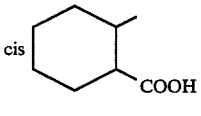

| Compound No. | R14 | Y | m.p. (°C.) | Physical property values (IR) |
|---|---|---|---|---|
| 138 | cis  (2-COOH cyclohexyl) | 6-OH | 304~6 | 1680, 1635, 1510, 1210, 960, 750 |
| 139 | " | 4-Cl | 176~8 | 1710, 1660, 1515, 1200, 945, 760 |
| 140 | " | 2-Me | 169~70 (decomposition) | 1700, 1650, 1435, 1215, 955, 760 |
| 141 | " | 4-OH | 305~7 | 1690, 1640, 1580, 1445, 1260, 760 |
| 142 | " | 4-OMe | 179~80 | 1670, 1430, 1250, 1050, 760 |
| 143 | " | 6-OMe | 197~8 (decomposition) | 1710, 1635, 1225, 1170, 960, 760 |
| 144 | " | 2-OH | 200 (decomposition) | 3290, 2910, 1690, 1445, 750 |

TABLE 2-5-continued
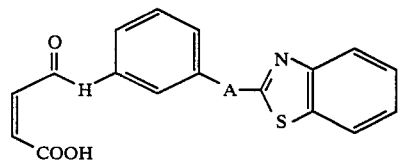
| Compound No. | R_{14} | Y | m.p. (°C.) | Physical property values (IR) |
|---|---|---|---|---|
| 145 | Et_2C(COOH)- | " | 195~6 | 3300, 2950, 1680, 1445, 965, 750 |
| 345 | cis 2-methyl cyclohexyl COONa | 6-OH | 214~7 | 1610, 1540, 1400, 1240, 955, 750 |
| 346 | " | 4-Cl | 168~72 | 1650, 1560, 1400, 1040, 755 |
| 347 | cis 2-methyl cyclohexyl COONa | 2-Me | 198~201 | 1635, 1560, 1405, 950, 755 |
| 348 | " | 4-OH | 254~7 | 1680, 1590, 1510, 1200, 820, 760 |
| 349 | " | 4-OMe | 234~6 | 1670, 1565, 1530, 1255, 755 |
| 350 | " | 6-OMe | 178~82 | 1650, 1550, 1500, 1400, 1235, 1030, 760 |
| 351 | " | 2-OH | 240 (decomposition) | 1680, 1540, 1190, 755 |
| 352 | Et_2C(COONa)- | " | 200~5 | 1550, 1430, 960, 750 |
TABLE 2-6
| Compound No. | A | m.p. (°C.) | Physical property values (IR) | Anti-SRS action [minimum effective conc. (M)] |
|---|---|---|---|---|
| 146 | —OCH_2— | 182~3 | 1700, 1625, 1575, 1490, 755 | |
| 147 | —CH_2OCH_2— | 138~40 | 1700, 1625, 1555, 1530, 953, 753 | |
| 148 | —CONH— | 217~9 | 1670, 1540, 1290, 1280, 750 | |
| 149 | —CH=CH—CONH— | 240~1 | 1705, 1685, 1620, 1580, 1540, 1265, 1160, 750 | |
| 150 | —NHCH_2— | 158~9 | 1690, 1610, 1490, 840, 750 | 2 × 10^{-7} |
| 151 | —(CH_2)_2— | 154~5 | 1700, 1620, 1550, 850, 760 | |

TABLE 2-7

$$R_{14}-CONH-\underset{\text{(m-position on phenyl)}}{C_6H_4}-CH_2CH_2-\underset{S}{\overset{N}{C}}=\underset{}{\overset{R_1}{C}}-R_2$$

| Compound No. | R$_{14}$ | R$_1$, R$_2$ | m.p. (°C.) | Physical property values | Anti-SRS action [minimum effective conc. (M)] |
|---|---|---|---|---|---|
| 152 | 2-methylphenyl-COOH | (benzene ring) | 151~3 | IR 1700, 1650, 1610, 1490, 1245 | |
| 153 | cis-2-COOH-cyclohexyl | " | 159~61 | IR 1710, 1640, 1530, 1440, 1180, 750 | |
| 154 | cis-2-COOH-cyclohexenyl | " | — | IR 1710, 1605, 1550, 1200, 730 NMR(CDCl$_3$)2.15~2.75(6H,m), 2.75~3.55(4H,m),5.57(2H,d),6.75~8.10(8H,m) | |
| 155 | —(CH$_2$)$_2$COOH | " | 161~2 | IR 1720, 1660, 1220, 1175, 760 | |
| 156 | 1-COOH-cyclohexyl | " | 158~9 | IR 1687, 1650, 1540, 755 | |
| 157 | Me$_2$C(COOH)— with Me | " | 163~4 | IR 1720, 1653, 1525, 1185, 755 | |
| 158 | CH$_3$CH$_2$CH$_2$CH(COOH)CH$_2$CH$_3$ | " | 130~1 | IR 1710, 1660, 1540, 1180, 755 | |

TABLE 2-7-continued
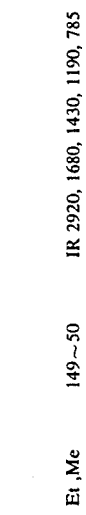
| Compound No. | R14 | m.p. (°C.) | R1,R2 | Physical property values | Anti-SRS action [minimum effective conc. (M)] |
|---|---|---|---|---|---|
| 159 | 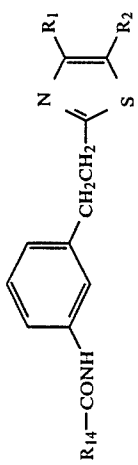 | 130~1 | " | IR 2910, 1690, 1640, 1430 | |
| 160 | | 125~6 | (CH3)2CH—,H | IR 1670, 1600, 1535, 1440, 1210, 780 | |
| 161 |  | 125~7 | " | IR 1690, 1660, 1545, 1440, 1210, 790 | |
| 162 | 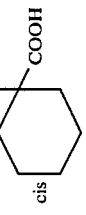 | 78~80 | (CH3)2CH—,H | IR 1710, 1660, 1605, 1440, 1175, 780 | |
| 163 | 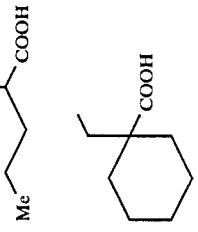 | 149~50 | Et,Me | IR 2920, 1680, 1430, 1190, 785 | |
| 164 | 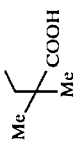 | 135~6 | " | IR 1677, 1540, 1430, 1190, 785 | |

TABLE 2-7-continued $$R_{14}-CONH-\underset{\text{(phenyl)}}{\phantom{XX}}-CH_2CH_2-\underset{S}{\overset{N}{\diagdown}}\overset{R_1}{\underset{R_2}{\diagup}}$$

| Compound No. | $R_{14}$ | $R_1, R_2$ | m.p. (°C.) | Physical property values | Anti-SRS action [minimum effective conc. (M)] |
|---|---|---|---|---|---|
| 165 | Me-CH(Et)-CH₂-CH(COOH)- (with Me branch) | " | 115~6 | IR 1705, 1655, 1605, 1400, 1175, 790 | |
| 188 | MeOOC— | | 112~3 | NMR(CDCl₃): δ = 3.3~3.7(4H,m),3.98(3H,s),6.90~8.08(8H,m),8.80(1H,broad s) | $2 \times 10^{-7}$ |
| 353 | CH₂=CH-CH(COONa)- | " | 98~100 (decomposition) | IR 1560, 1435, 860, 760 | |
| 354 | o-(COONa)-C₆H₄-CH₂- | " | 116~20 | IR 1650, 1580, 1560, 1385, 755 | |
| 355 | cis-2-(COONa)-cyclohexyl-CH₂- | " | 223~7 | IR 1660, 1560, 1405, 755 | |
| 356 | cis-2-(COONa)-cyclohex-4-enyl-CH₂- | " | 201~10 | IR 1660, 1550, 1425, 1200, 755 | |
| 357 | NaOOC(CH₂)₂— | " | 145~8 | IR 1650, 1550, 1420, 750 | |

TABLE 2-7-continued $$R_{14}-CONH-\underset{CH_2CH_2}{\underset{|}{\bigcirc}}-\underset{S}{\overset{N}{\diagup}}\underset{R_2}{\overset{R_1}{\diagdown}}$$

| Compound No. | R14 | R1, R2 | m.p. (°C.) | Physical property values | Anti-SRS action [minimum effective conc. (M)] |
|---|---|---|---|---|---|
| 358 | cyclohexyl-COONa with ethyl | " | 92~102 | IR 1655, 1545, 1435, 755 | $10^{-8}$ |
| 359 | Me-C(Me)(COONa)- | " | 80~85 | IR 2950, 1655, 1550, 1430, 955 | |
| 360 | Me-CH(Et)-CH2-CH(COONa)-Et | " | 70~80 | IR 2950, 1650, 1550, 1410, 950 | |
| 361 | Me-(CH2)4-CH(COONa)-Et | cyclohexadienyl | 55~60 | IR 2910, 1645, 1545, 1400, 750 | |
| 362 | cyclohexyl-COONa with ethyl | —CH(CH3)2, H | 96~98 | IR 1650, 1540, 1440, 1205, 735 | $2 \times 10^{-8}$ |
| 363 | Me-C(Me)(COONa)- | " | 82~3 | IR 1650, 1540, 1400, 1105, 735 | |

TABLE 2-7-continued
$$R_{14}-CONH-\underset{\text{CH}_2\text{CH}_2}{\bigcirc}\underset{S}{\overset{N}{\diagdown}}\underset{R_2}{\overset{R_1}{=}}$$
| Compound No. | R14 | R1,R2 | m.p. (°C.) | Physical property values | Anti-SRS action [minimum effective conc. (M)] |
|---|---|---|---|---|---|
| 364 | 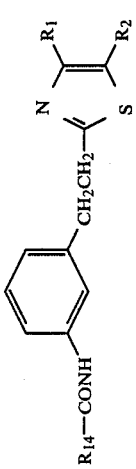 | " | 67~70 | IR 1650, 1540, 1400, 1180, 735 | |
| 365 | 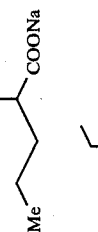 | Et,Me | 95~100 | IR 2910, 1650, 1545, 1300, 780 | |
| 366 | 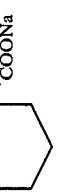 | " | 75~80 (decomposition) | IR 2950, 1650, 1540, 1435, 875, 780 | $5 \times 10^{-8}$ |
| 367 | 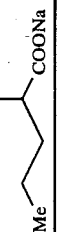 | " | 120~1 (decomposition) | IR 2950, 1650, 1545, 1435, 1300, 780 | |

TABLE 2-8

HOOC(CH₂)₃NH— [phenyl]—A—C(=N)(S)—C(R₁)=C(R₂)

| Compound No. | A | R₁, R₂ | m.p. (°C.) | Physical property values |
|---|---|---|---|---|
| 171 | —CH=CH— | —(CH₂)₂CH₃, Et | 115~6 | IR 1705, 1590, 1330, 1190, 940, 678 |
| 172 | " | —CH(CH₃)₂, H | 112~3 | IR 1690, 1590, 1405, 1185, 945, 775 |
| 173 | " | (4-Me-phenyl), H | 83~5 | IR 1670, 1590, 1390, 945, 730 |
| 174 | " | Et, Me | 129~30 | IR 1705, 1600, 1330, 1190, 940, 780 |
| 175 | " | —(CH₂)₄CH₃, H | 127~8 | IR 1700, 1590, 1330, 1180, 965, 715 |
| 176 | " | —C(CH₃)₃, H | 106~7 | IR 1700, 1600, 1510, 950, 760 |
| 177 | " | Et, H | 115~6 | IR 1695, 1590, 1190, 950, 780 |
| 178 | " | —(CH₂)₃CH₃, H | 96~9 | IR 1705, 1590, 1330, 1190, 945 |
| 179 | " | —(CH₂)₅CH₃, H | 113~4 | IR 1710, 1600, 1330, 1190, 720 |
| 180 | " | —(CH₂)₆CH₃, H | 108~9 | IR 1710, 1590, 1330, 720 |
| 181 | —CH₂OCH₂— | (cyclohexenyl) | — | IR 1685, 1600, 1100, 755<br>NMR (CDCl₃): δ = 1.7~2.7(5H, m), 3.15(2H, t), 4.58(2H, s), 4.9(2H, s), 6.4~8.1(9H, m) |
| 182 | —OCH₂— | " | 120~3 | IR 1705, 1600, 1250, 1180 |

TABLE 2-9

W—[phenyl]—CH=CH—C(=N)(S)—C(R₁)=C(R₂)

| Compound No. | W | R₁, R₂ | m.p. (°C.) | Physical Property values | Anti-SRS action [minimum effective conc. (M)] |
|---|---|---|---|---|---|
| 197 | EtOOC(CH₂)₄— | C₆H₅, H | 78~9 | IR 1720, 1480, 1180, 960, 740 | |
| 198 | " | Me, Me | — | IR 1720, 1540, 1440, 1175, 950, 780<br>NMR(CDCl₃): δ = 1.25(3H,t), 1.5~1.9(4H, m), 2.3(s,6H), 2.2~2.9(m,4H), 4.1(2H,q), 6.9~7.4(6H,m) | |
| 200 | EtOOCCH₂NH— | (cyclohexenyl) | 121~4 | IR 1720, 1600, 1220, 950, 758 | |
| 201 | EtOOC(CH₂)₄NH— | " | 108~9 | IR 1710, 1595, 1180, 750 | |
| 202 | " | C₆H₅, H | 110~1 | IR 1710, 1595, 1470, 1185, 720 | |
| 203 | EtOOC(CH₂)₃NH— | Me, Me | — | IR 1710, 1595, 1480, 1280, 1190, 755<br>NMR(CDCl₃): δ = 1.25(3H,t), 2.03(2H,m), 2.35 (6H,s), 2.25~2.50(2H,m), 3.20(2H,m), 4.16(2H,q), 6.28~7.33(6H,m) | |
| 204 | EtOOC(CH₂)₃NH— | C₆H₅, H | 89.5~90 | NMR(CDCl₃): δ = 1.25(3H,t), 1.78~2.48(4H,m), 3.20(2H,m), 4.13(2H,q), 6.38~8.00(12H,m) | |
| 207 | EtOOC(CH₂)₃O— | (cyclohexenyl) | 135~7 | IR 1720, 1590, 1273, 1190, 770 | |

TABLE 2-9-continued

| Compound No. | W | R₁, R₂ | m.p. (°C.) | Physical Property values | Anti-SRS action [minimum effective conc. (M)] |
|---|---|---|---|---|---|
| 208 | EtOOC(CH₂)₄O— | " | 72~3 | IR 1720, 1590, 1180, 970, 755 | |
| 209 | EtOOC(CH₂)₃O— | C₆H₅,H | 85~86 | IR 1725, 1265, 1180, 945, 730 | |
| 210 | cyclohexyl-CH₂-O— with COOMe | phenyl | — | IR 1720, 1570, 1140, 950, 760 | |
| 211 | Me₂C(Me)CH₂-O— with COOMe | " | — | NMR(CDCl₃): δ = 0.72~2.97(10H,m), 3.62(3H,s),3.40~4.21(2H,m), 6.62~7.99(10H,m) IR 1720, 1570, 1145, 950, 760 | |
| 212 | benzyl-O— with COOMe (ortho) | " | 87~8 | NMR(CCl₄): δ = 1.26(6H,s),1.98(2H,t), 3.62(3H,s),3.92(2H,t), 6.55~7.95(10H,m) IR 1710, 1570, 1260, 1040, 740 | |
| 373 | NaOOC(CH₂)₄NH— | " | 239~40 | IR 2925, 1560, 1430, 1310, 955, 750 | |
| 374 | " | C₆H₅—,H | 270~1 | IR 2925, 1560, 1430, 960, 730 | 2 × 10⁻⁷ |
| 375 | phenyl-NH— with COONa (ortho) | phenyl | 215~8 | IR 1570, 1510, 1380, 1280, 750 | 2 × 10⁻⁷ |
| 394 | NaOOC(CH₂)₂O— | " | 239~41 (decomposition) | IR 1570, 1420, 1200, 950, 750 | |
| 395 | NaOOC(CH₂)₃O— | " | 255~8 | IR 1550, 1420, 1170, 940, 750 | 5 × 10⁻⁷ |
| 397 | NaOOCCH₂NH— | " | 257~60 | IR 1595, 1570, 1410, 940, 745 | |
| 398 | NaOOC(CH₂)₄NH— | " | 239~40 | IR 1595, 1555, 1430, 955, 750 | |
| 399 | " | C₆H₅—,H | 270~1 | IR 1600, 1560, 1430, 960, 730 | |
| 401 | NaOOCCH₂O— | phenyl | >320 | IR 1590, 1425, 940, 745 | |
| 402 | NaOOC(CH₂)₃O— | " | 260~2 | IR 1550, 1420, 940, 750 | |
| 403 | NaOOC(CH₂)₃O— | C₆H₅—,H | 289~90 | IR 1545, 1415, 950, 730 | |
| 404 | NaOOC(CH₂)₄O— | phenyl | 216~9 | IR 1560, 1430, 1270, 750 | |
| 405 | cyclohexyl-CH₂-O— with COONa | " | 230 (decomposition) | IR 2920, 1620, 1560, 1440, 750 | |
| 406 | Me₂C(Me)CH₂-O— with COONa | " | 198~203 | IR 1575, 1520, 1480, 1445, 1165, 950, 760 | |

TABLE 2-9-continued

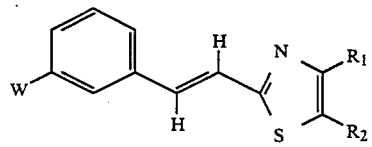

| Compound No. | W | $R_1, R_2$ | m.p. (°C.) | Physical Property values | Anti-SRS action [minimum effective conc. (M)] |
|---|---|---|---|---|---|
| 407 | ![2-(CH2O-)C6H4-COONa] | " | ~250 (decomposition) | IR 1545, 1400, 1200, 1030, 740 | $5 \times 10^{-8}$ |
| 409 | $NaOOC(CH_2)_3-$ | " | >350 | IR 1615, 1425, 1345, 1090, 1070, 823 | |
| 410 | $NaOOC(CH_2)_4-$ | " | 227~30 | IR 1560, 1410, 945, 750 | |
| 411 | $NaOOC(CH_2)_5-$ | " | 278~82 | IR 1560, 1430, 1310, 950, 750 | $10^{-5}$ |
| 412 | $NaOOC(CH_2)_4-$ | $C_6H_5-,H$ | 265~8 | IR 1550, 1440, 960, 730 | |
| 413 | " | Me, Me | 285~90 | IR 1560, 1410, 950, 765 | |
| 431 | [Me2C(COOEt)CH2CH2O-] | $-CH(CH_3)_2,H$ | oil | NMR(CDCl$_3$): δ = 1.4(6H,s),1.45(6H,d), 1.4(3H,t),2.15(2H,t),2.9~3.4(1H,m), 3.95~4.42(4H,m),6.7~7.42(7H,m) IR 1720, 1590, 1260, 1145, 1020 | |
| 432 | [Et2C(COOMe)CH2CH2O-] | $-CH(CH_3)_2,H$ | oil | NMR(CDCl$_3$): δ = 1.33(6H,d),1.69(4H,q), 1.85(6H,t),2.07(2H,t),2.80~ 3.40(1H,m),3.65(3H,s),3.92 (2H,t),6.66~7.35(7H,m) IR 1720, 1590, 1240, 1140, 1040 | |
| 433 | [Et(Me)C(COOMe)CH2CH2O-] | " | oil | NMR(CDCl$_3$): δ = 0.66~1.12(6H,m), 1.3~1.9 (4H,m),1.95~2.30(2H,t), 3.67(3H,s),3.7~4.28(2H,m), 6.69~8.10(10H,m) IR 1720, 1240, 1140, 1030, 760 | |
| 434 | [2-(EtO-)C6H4-COONa] | " | >300 | IR 1580, 1380, 1210, 945, 750 | $2 \times 10^{-8}$ |
| 435 | [2-(EtNH-)C6H4-COONa] | " | 287~8 | IR 1610, 1505, 1380, 950, 750 | $10^{-7}$ |
| 436 | [Me2C(COONa)CH2CH2OMe] | " | 198~203 | IR 1575, 1520, 1445, 1040, 760 | $10^{-8}$ |
| 438 | [2-(CH2O-)C6H4-COOH] | $-CH(CH_3)_2,H$ | 179~81 | IR 1690, 1565, 1265, 1025, 965 | |
| 439 | [Et2C(COOH)CH2CH2O-] | $-CH(CH_3)_2,H$ | 106~8 | IR 1690, 1590, 1220, 965, 780 | $2 \times 10^{-9}$ |

TABLE 2-9-continued

| Compound No. | W | R₁, R₂ | m.p. (°C.) | Physical Property values | Anti-SRS action [minimum effective conc. (M)] |
|---|---|---|---|---|---|
| 440 | Et₂C(NH—)(COOH)CH₂ | " | oil | NMR(CDCl$_3$): δ = 0.92(6H,t),1.35(6H,d), 1.82(4H,q),2.9~3.6(1H,m), 3.35(2H,s),6.4~7.34(7H,m) IR 1685, 1590, 1250, 950, 770 | |
| 441 | Et₂C(O—)(COOH)CH₂ | phenyl (fused) | 129~30 | IR 1680, 1585, 1440, 1210, 750 | $5 \times 10^{-8}$ |
| 442 | Et₂C(NH—)(COOH)CH₂ | " | 95~6 | IR 1665, 1570, 1280, 1200, 950 | |
| 443 | Et₂C(O—)(COOH)CH₂ | —(CH$_2$)$_2$CH$_3$, H | 64~5 | IR 1690, 1440, 1260, 955 | |
| 444 | (CH$_3$)$_2$CHCH$_2$C(Et)(COOH)CH$_2$O— | —CH(CH$_3$)$_2$, H | 104~5 | IR 1700, 1260, 1200, 1150, 960 | |

TABLE 2-10

| Compound No. | A | m.p. (°C.) | Physical property values (IR) | Anti-SRS action [minimum effective conc. (M)] |
|---|---|---|---|---|
| 368 | —OCH$_2$— | 115~7 | 1660, 1560, 1440, 750 | $10^{-7}$ |
| 369 | —CH$_2$OCH$_2$— | 67~70 | 1570, 1440, 1355, 750 | $10^{-5}$ |
| 370 | —CONH— | 277~80 | 1665, 1540, 1435, 1275, 745 | |
| 371 | —CH=CH—CONH— | 341~4 | 1670, 1545, 1435, 1260, 1070, 745 | |
| 372 | —NHCH$_2$— | 134~8 | 1660, 1560, 1430, 1305, 850, 755 | |

TABLE 2-11

NaOOC(CH₂)₃NH—[phenyl]—A—[thiazole with R₁, R₂]

| Compound No. | A | R₁, R₂ | m.p. (°C.) | Physical property values (IR) | Anti-SRS action [minimum effective conc. (M)] |
|---|---|---|---|---|---|
| 376 | —(CH₂)₂— | (cyclohexenyl) | 148~50 | 2900, 1600, 1550, 1430, 1100, 760 | 5 × 10⁻⁷ |
| 377 | —CH=CH— | Me, Me | 133~5 | 1600, 1555, 1410, 950, 770 | 2 × 10⁻⁷ |
| 378 | " | (cyclohexenyl-Me) | 179~82 | 1560, 1400, 1305, 940, 770 | |
| 379 | " | (cyclohexenyl-Cl) | 167~70 | 1625, 1540, 1405, 940, 775 | |
| 380 | " | (phenyl-Cl), H | 237~9 | 1560, 1410, 1100, 958, 830, 745 | |
| 381 | " | (phenyl-Me), H | 205~7 | 1560, 1420, 950, 740, 690 | |
| 382 | " | Et, Me | 144~6 | 1540, 1410, 1330, 950, 765 | |
| 383 | " | —CH(CH₃)₂, H | 125~9 | 1560, 1400, 1300, 940, 765 | |
| 384 | " | —(CH₂)₄CH₃, H | 165~70 | 1625, 1550, 1405, 950, 768 | |
| 385 | " | —(CH₂)₂CH₃, Et | 154~5 | 1555, 1430, 950, 765 | |
| 386 | —CH=CH— | —C(CH₃)₃, H | 155~7 | 1560, 1410, 1100, 950, 745 | |
| 387 | " | Et, H | 138~40 | 1550, 1410, 950, 765 | 10⁻⁸ |
| 388 | " | —(CH₂)₂CH₃, H | 133~5 | 1555, 1410, 953, 770, 685 | |
| 389 | " | —(CH₂)₃CH₃, H | 123~7 | 1595, 1560, 1435, 1410, 955, 770 | 10⁻⁷ |
| 390 | " | —(CH₂)₅CH₃, H | 112~5 | 1560, 1410, 950, 770, 685 | |
| 391 | " | —(CH₂)₆CH₃, H | 153~4 | 1550, 1410, 950, 770 | |
| 392 | —OCH₂— | (cyclohexenyl) | 125~30 | 1615, 1570, 1210, 753 | |
| 393 | —CH₂OCH₂— | " | 139~45 | 1675, 1600, 1460, 1400, 755 | |
| 400 | —CH=CH— | C₆H₅—, H | 270~6 | 1600, 1550, 1430, 955, 730 | |

TABLE 2-12

| Compound No. | Structural Formula | m.p. (°C.) | Physical property values (IR) |
|---|---|---|---|
| 205 | EtOOC(CH₂)₃NH—[phenyl]—OCH₂—[benzothiazole] | 98~9 | 1715, 1600, 1250, 1175, 750 |

TABLE 2-12-continued

| Compound No. | Structural Formula | m.p. (°C.) | Physical property values (IR) |
|---|---|---|---|
| 408 | NaOOC(CH₂)₃O—[phenyl]—CH₂CH₂—[benzothiazole] | 207~8 | 1557, 1430, 1165, 1040, 750 |
| 420 | Tris.HOOCCONH—[phenyl]—CH₂CH₂—[benzothiazole] | 224~5 | 1660, 1520, 1440, 750 |
| 421 | NMG.HOOC(CH₂)₃O—[phenyl]—CH=CH—[benzothiazole] | 108~9 | 1570, 1430, 1085, 750 |

TABLE 3

| Test compound | | Anti-SRS action [Minimum effective conc. (M)] |
|---|---|---|
| Compound | Example | |
| 1 | 1 | $5 \times 0^{-8}$ |
| 189 | 9 | $10^{-6}$ |
| 199 | 13 | $2 \times 10^{-7}$ |
| 213 | 17 | $5 \times 10^{-8}$ |
| 398 | 19 | $2 \times 10^{-7}$ |
| 414 | 21 | $10^{-6}$ |
| 422 | 23 | $10^{-6}$ |
| 423 | 24 | $10^{-5}$ |
| 424 | 25 | $5 \times 10^{-7}$ |
| 426 | 27 | $2 \times 10^{-7}$ |

TABLE 4

| Test Compound | | Airway resistance increase inhibition (%) |
|---|---|---|
| Compound No. | Dosage (mg/kg) | |
| 213 | 30 | 51 |
| 223 | 3 | 87 |
| 227 | 3 | 71 |
| 272 | 10 | 37 |
| 297 | 10 | 62 |
| 353 | 30 | 79 |
| 396 | 3 | 55 |

TABLE 5

| Compound No. | Acute toxicity value ($LD_{50}$ mg/kg) |
|---|---|
| 2 | >3000 |
| 26 | >3000 |
| 213 | >3000 |
| 216 | >3000 |
| 232 | 3000 |
| 247 | >3000 |
| 248 | >3000 |
| 249 | 1000 ~ 2000 |
| 281 | >3000 |
| 300 | 1000 ~ 2000 |
| 303 | 2000 |
| 313 | 1560 |
| 314 | 2000 ~ 3000 |
| 315 | 1000 ~ 2000 |
| 317 | 1032 |
| 324 | 1380 |
| 325 | 2000 |

TABLE 5-continued

| Compound No. | Acute toxicity value ($LD_{50}$ mg/kg) |
|---|---|
| 326 | <3000 |
| 353 | 3308 |
| 355 | 1928 |
| 382 | 1928 |
| 396 | 2000 ~ 3000 |
| 418 | <3000 |

We claim:

1. A thiazole derivative represented by the following formula and a pharmaceutically acceptable salt thereof:

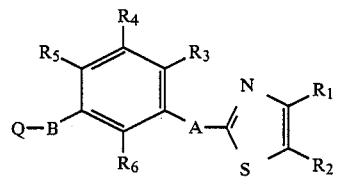

wherein $R_1$ and $R_2$ each independently represent a hydrogen atom, an alkyl group having 1 to 8 carbon atoms, a lower alkoxycarbonyl group or a phenyl group which is unsubstituted or substituted with a halogen atom, a lower alkoxy group, a lower alkoxycarbonyl group or an alkyl group of 1 to 3 carbon atoms or wherein $R_1$ and $R_2$ cooperate to represent a tetramethylene group corresponding to a fused cyclohexane ring or a butadienylene group which is unsubstituted or substituted with a halogen atom, a lower alkoxy group, a lower alkoxycarbonyl group or an alkyl group having 1 to 3 carbon atoms corresponding to a fused benzene ring; $R_3$, $R_4$, $R_5$ and $R_6$ each independently represent a hydrogen atom, a hydroxyl group, a lower alkoxy group, an alkyl group having 1 to 3 carbon atoms or a halogen atom; A is a linking group selected from the group consisting of —CH=CH—, —CH₂CH₂—, —CH=CHCONH— and —CH₂OCH₂—; B is a group selected from the group consisting of (a) —(CH₂)ₙ—CONH—, wherein n is an integer of 0-3, (b)

—$(CH_2)_n$—NH—, wherein n is an integer of 1-4, (c)
—$(CH_2)_n$—O—, wherein n is an integer of 1-4, (d)
—$(CH_2)_n$—, wherein n is an integer of 2-5,

  (e)

wherein $R_7$ and $R_8$ each independently represents a hydrogen atom or an alkyl group having 1 to 3 carbon atoms as defined above,

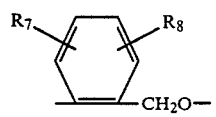  (f)

wherein $R_7$ and $R_8$ have the same meanings as defined above,

  (g)

wherein $R_7$ and $R_8$ have the same meanings as defined above,

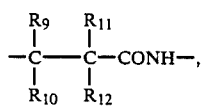  (h)

wherein $R_9$, $R_{10}$, $R_{11}$ and $R_{12}$ each independently represent a hydrogen atom, a phenyl group or an alkyl group having 1 to 6 carbon atoms,

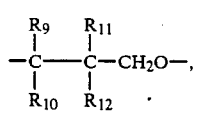  (i)

wherein $R_9$, $R_{10}$, $R_{11}$ and $R_{12}$ have the same meanings as defined above,

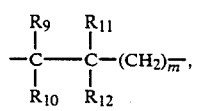  (j)

wherein $R_9$, $R_{10}$, $R_{11}$ and $R_{12}$ have the same meanings as defined above and m ranges from 0 to 3,

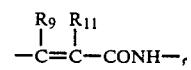  (k)

wherein $R_9$ and $R_{11}$ have the same meanings as defined above,

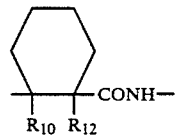  (l)

wherein $R_{10}$ and $R_{12}$ have the same meanings as defined above,

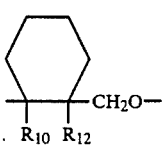  (m)

wherein $R_{10}$ and $R_{12}$ have the same meanings as defined above,

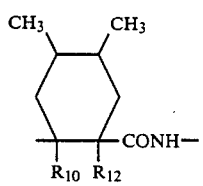  (n)

wherein $R_{10}$ and $R_{12}$ have the same meanings as defined above,

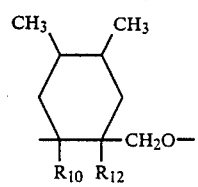  (o)

wherein $R_{10}$ and $R_{12}$ have the same meanings as defined above,

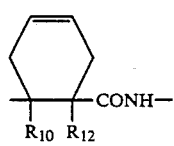  (p)

wherein $R_{10}$ and $R_{12}$ have the same meanings as defined above,

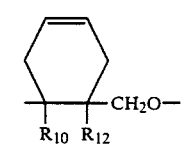  (q)

wherein $R_{10}$ and $R_{12}$ have the same meanings as defined above,

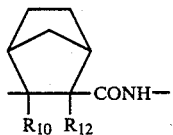 (r)

wherein $R_{10}$ and $R_{12}$ have the same meanings as defined above,

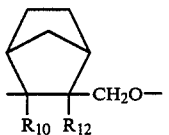 (s)

wherein $R_{10}$ and $R_{12}$ have the same meanings as defined above,

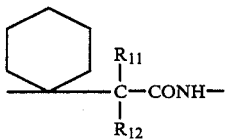 (t)

wherein $R_{11}$ and $R_{12}$ have the same meanings as defined above, and

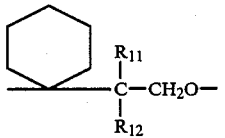 (u)

wherein $R_{11}$ and $R_{12}$ have the same meanings as defined above and Q represents a carboxyl group, a lower alkoxy group, a hydroxyl group, an alkoxycarbonyl group having 2 to 6 carbon atoms or a 5-tetrazolyl group.

2. The thiazole derivative and the pharmaceutically acceptable salt thereof according to claim 1, wherein said group B has the formkla:

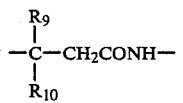

wherein $R_9$ and $R_{10}$ each independently represent an alkyl group of 1 to 6 carbon atoms.

3. A leukotriene antagonist composition comprising: a pharmaceutically effective amount of a thiazole derivative represented by the following formula or a pharmaceutically acceptable salt thereof as the active ingredient:

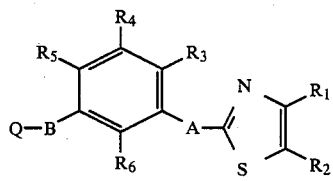

wherein $R_1$ and $R_2$ each independently represent a hydrogen atom, an alkyl group having 1 to 8 carbon atoms, a lower alkoxycarbonyl group or a phenyl group which is unsubstituted or substituted with a halogen atom, a lower alkoxy group, a lower alkoxycarbonyl group or an alkyl group having 1 to 3 carbon atoms or wherein $R_1$ and $R_2$ cooperate to represent a tetramethylene group corresponding to a fused cyclohexane ring or a butadienylene group which is unsubstituted or substituted with a halogen atom, a lower alkoxy group, a lower alkoxycarbonyl group or an alkyl group having 1 to 3 carbon atoms corresponding to a fused benzene ring; $R_3$, $R_4$, $R_5$ and $R_6$ each independently represent a hydrogen atom, a hydroxyl group, a lower alkoxy group, an alkyl group having 1 to 3 carbon atoms or a halogen atom; A is a linking group selected from the group consisting of —CH=CH—, —CH$_2$CH$_2$—, —CH=CH-CONH— and —CH$_2$OCH$_2$—; B is a group selected from the group consisting of (a) —(CH$_2$)$_n$—CONH—, wherein n is an integer of 1-3, (b) —(CH$_2$)$_n$—NH—, wherein n is an integer of 1-4, (c) —(CH$_2$)$_n$—O—, wherein n is an integer of 1-4, (d) —(CH$_2$)$_n$—, wherein n is an integer of 2-5,

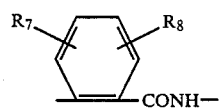 (e)

wherein $R_7$ and $R_8$ each independently represent a hydrogen atom or an alkyl group having 1 to 3 carbon atoms as defined above,

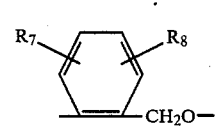 (f)

wherein $R_7$ and $R_8$ have the same meanings as defined above,

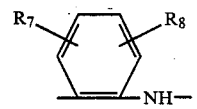 (g)

wherein $R_7$ and $R_8$ have the same meanings as defined above,

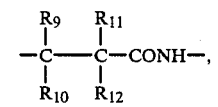 (h)

wherein $R_9$, $R_{10}$, $R_{11}$ and $R_{12}$ each independently represent a hydrogen atom, a phenyl group or an alkyl group having 1 to 6 carbon atoms,

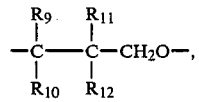 (i)

wherein $R_9$, $R_{10}$, $R_{11}$ and $R_{12}$ have the same meanings as defined above,

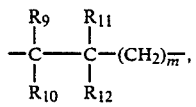 (j)

wherein $R_9$, $R_{10}$, $R_{11}$ and $R_{12}$ have the same meanings as defined above and m ranges from 0 to 3,

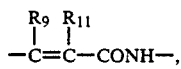 (k)

wherein $R_9$ and $R_{11}$ have the same meanings as defined above,

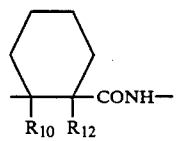 (l)

wherein $R_{10}$ and $R_{12}$ have the same meanings as defined above,

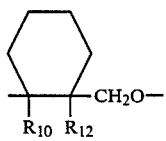 (m)

wherein $R_{10}$ and $R_{12}$ have the same meanings as defined above,

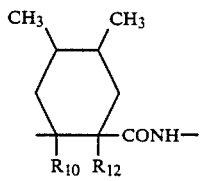 (n)

wherein $R_{10}$ and $R_{12}$ have the same meanings as defined above,

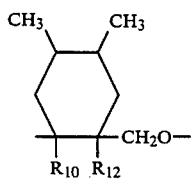 (o)

wherein $R_{10}$ and $R_{12}$ have the same meanings as defined above,

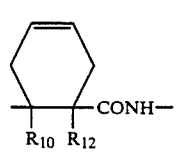 (p)

wherein $R_{10}$ and $R_{12}$ have the same meanings as defined above,

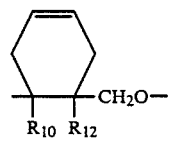 (q)

wherein $R_{10}$ and $R_{12}$ have the same meanings as defined above,

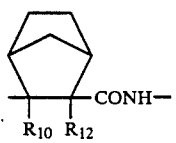 (r)

wherein $R_{10}$ and $R_{12}$ have the same meanings as defined above,

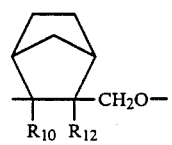 (s)

wherein $R_{10}$ and $R_{12}$ have the same meanings as defined above,

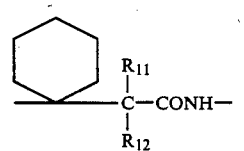 (t)

wherein $R_{11}$ and $R_{12}$ have the same meanings as defined above, and

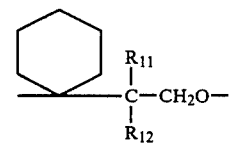 (u)

wherein $R_{11}$ and $R_{12}$ have the same meanings as defined above; and Q represents a carboxyl group, a lower alkoxy group, a hydroxyl group, an alkoxycarbonyl group having 2 to 6 carbon atoms or a 5-tetrazolyl group, in combination with a pharmaceutically acceptable excipient.

4. The leukotriene antagonist composition of claim 3, wherein said group B has the formula:

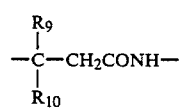

wherein $R_9$ and $R_{10}$ each independently represent an alkyl group of 1 to 6 carbon atoms.

5. A leukotriene antagonist composition, comprising:

a pharmaceutically effective amount of a thiazole derivative represented by the following formula or a pharmaceutically acceptable salt thereof as the active ingredient:

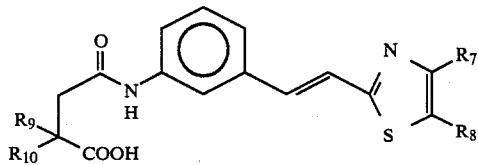

wherein $R_7$ and $R_8$ each independently represent a hydrogen atom, an alkyl group having 1-8 carbon atoms or cooperatively represent a butadienylene group which is unsubstituted or substituted with a halogen atom, a lower alkoxy group, a lower alkoxycarbonyl group or an alkyl group having 1-3 carbon atoms corresponding to a fused benzene ring; and $R_9$ and $R_{10}$ each independently represent a hydrogen atom or an alkyl group having 1-6 carbon atoms.

6. A method of therapeutically treating an allergic disorder in which leukotriene is released, comprising: administering to a host subject a leukotriene antagonistic effective amount of the thiazole derivative of claim 1.

* * * * *